US012728032B2

(12) United States Patent
Castillo et al.

(10) Patent No.: US 12,728,032 B2
(45) Date of Patent: Sep. 8, 2026

(54) ANATOMICAL CLOSING SYSTEM FOR HEALTH AND WELLNESS

(71) Applicant: Intake Breathing Technology, LLC, Santa Barbara, CA (US)

(72) Inventors: Daniel J. Castillo, Laguna Beach, CA (US); James D. Castillo, Santa Barbara, CA (US)

(73) Assignee: Intake Breathing Technology, LLC, Santa Barbara, CA (US)

( * ) Notice: Subject to any disclaimer, the term of this patent is extended or adjusted under 35 U.S.C. 154(b) by 0 days.

(21) Appl. No.: 19/188,622

(22) Filed: Apr. 24, 2025

(65) Prior Publication Data

US 2025/0332023 A1 Oct. 30, 2025

Related U.S. Application Data

(60) Provisional application No. 63/708,683, filed on Oct. 17, 2024, provisional application No. 63/639,144, filed on Apr. 26, 2024.

(51) Int. Cl.

| | |
|---|---|
| ***A61F 5/56*** | (2006.01) |
| ***A61F 13/0246*** | (2024.01) |
| ***A61F 13/12*** | (2006.01) |

(52) U.S. Cl.
CPC .............. *A61F 5/56* (2013.01); *A61F 13/025* (2013.01); *A61F 13/122* (2013.01)

(58) Field of Classification Search
CPC .. A61F 5/56; A61F 5/58; A61F 5/0003; A61F 5/0006; A61F 13/122; A61F 5/37;
(Continued)

(56) References Cited

U.S. PATENT DOCUMENTS 4,774,935 A * 10/1988 Aronsohn ................. A61F 5/30
606/204.45
9,283,106 B2 3/2016 Castillo
(Continued)

FOREIGN PATENT DOCUMENTS

| | | | | |
|---|---|---|---|---|
| EP | 3727218 B1 | 3/2023 | | |
| FR | 2898040 A1 * | 9/2007 | ........... | A61F 5/3753 |
| JP | 7176723 B2 | 11/2022 | | |

OTHER PUBLICATIONS

Lafosse et al., FR 2898040 A1 (translation).*
(Continued)

*Primary Examiner* — Victoria Hicks Fisher
(74) *Attorney, Agent, or Firm* — Stetina Garred Brucker & Newboles

(57) ABSTRACT

A system for holding a portion of a user's body in a desired configuration includes a pair of tabs, each including a flexible body and a metallic element. The tabs are configured to be attachable to the user's body in spaced relation to each other. The system additionally includes a band having a main body and at least two magnets coupled to the main body. At least one of the at least two magnets is coupled to a respective one of the pair of distal portions of the band, with each magnet being configured to be magnetically attractable to one of the pair of tabs to facilitate magnetic attraction. The main body and the pair of tabs are configured to be mechanically coupled to the pair of tabs when the magnets of the band are magnetically coupled to the pair of tabs.

18 Claims, 20 Drawing Sheets

(58) Field of Classification Search
CPC .......... A61F 5/3707; A61F 5/08; A61B 17/08; A61B 2017/081; A61B 17/085; A61B 2017/086; A61B 2017/00876; A61C 7/06; A61M 29/00
See application file for complete search history.

(56) References Cited

U.S. PATENT DOCUMENTS 9,510,969 B2 * 12/2016 Castillo .................. A61F 9/026
9,675,493 B2 6/2017 Castillo
10,556,095 B2 2/2020 Castillo
10,675,174 B2 6/2020 Castillo
2010/0083971 A1 4/2010 Webster et al.
2015/0051530 A1 * 2/2015 Noda .................. A61B 17/085
602/41
2015/0173934 A1 * 6/2015 Castillo .................... A61F 5/08
606/204.45
2017/0028162 A1 2/2017 Leeflang et al.
2023/0390030 A1 * 12/2023 Boronkay ............ A61C 8/0096

OTHER PUBLICATIONS

Thomas, Shane; PCT International Search Report and Written Opinion regarding PCT/US2025/026476; dated Jun. 17, 2025; 15 pages.

* cited by examiner 213
202
200
214
213
204

200
206
22
202
213
213
216
214
206
22

212
208
213
206, 206a
206, 206b
208
214
210

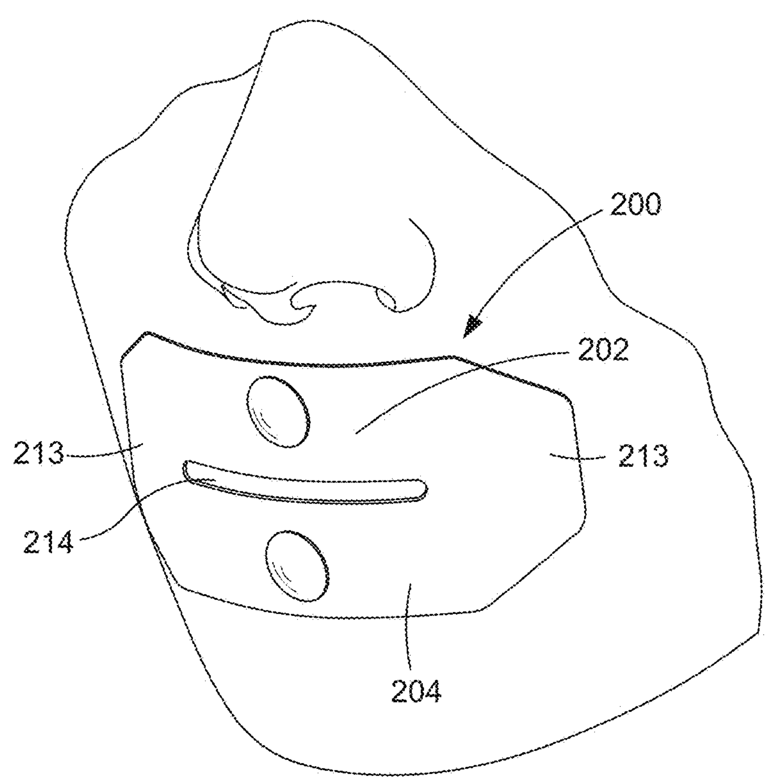
FIG. 24
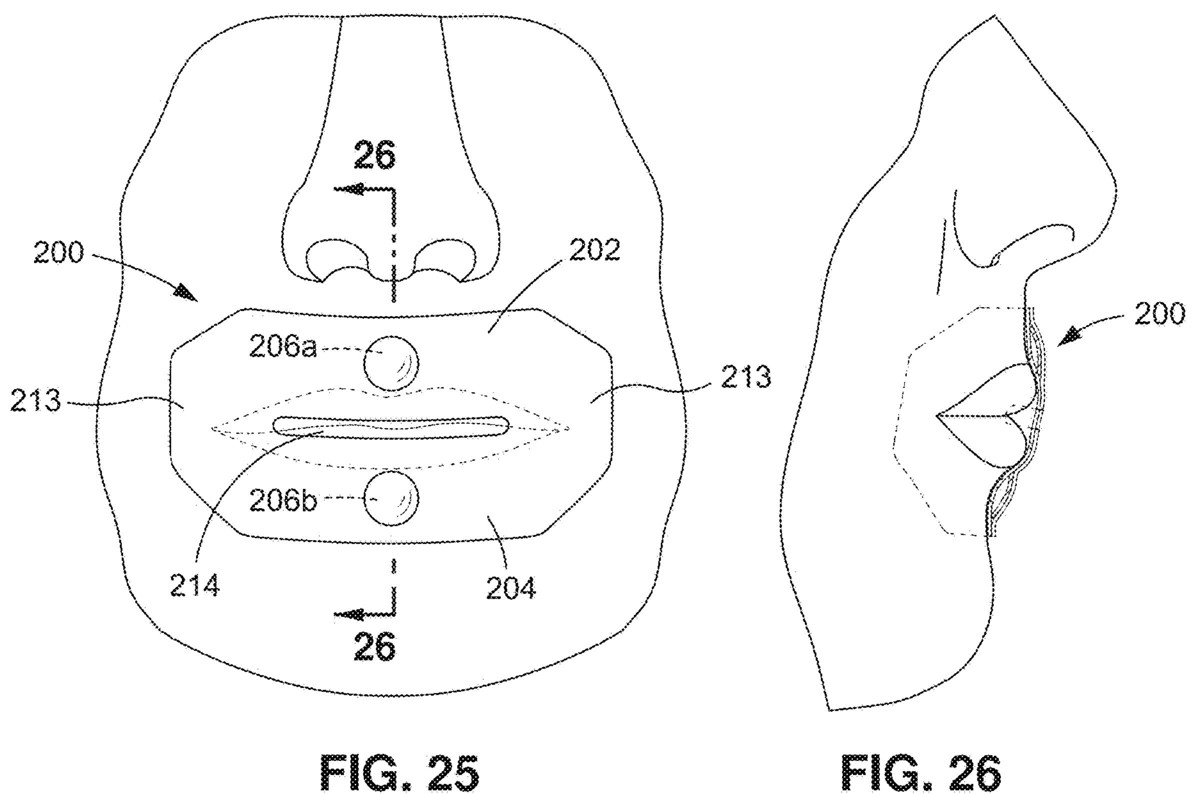
FIG. 25
FIG. 26

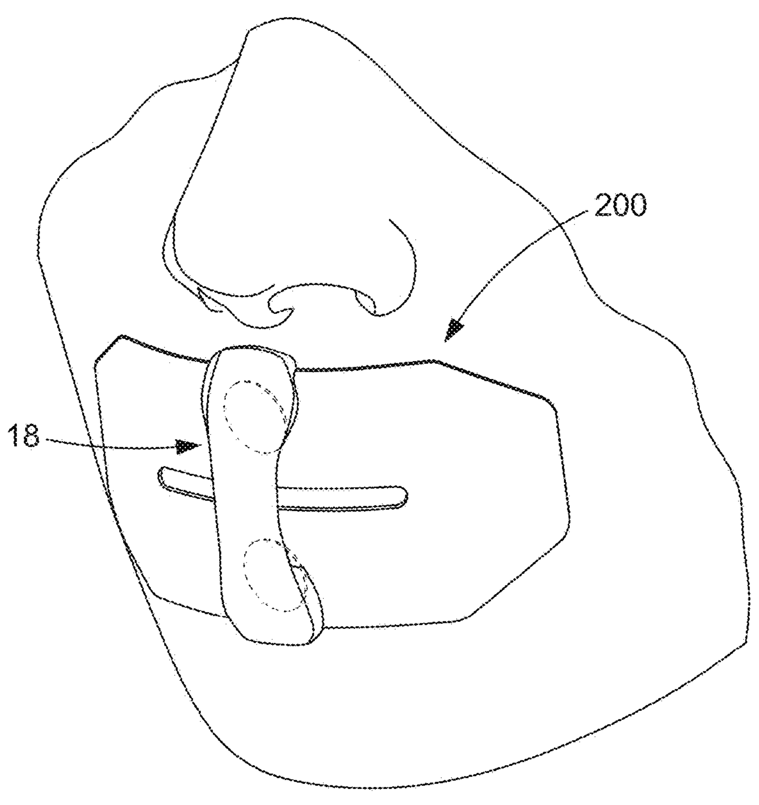
FIG. 27
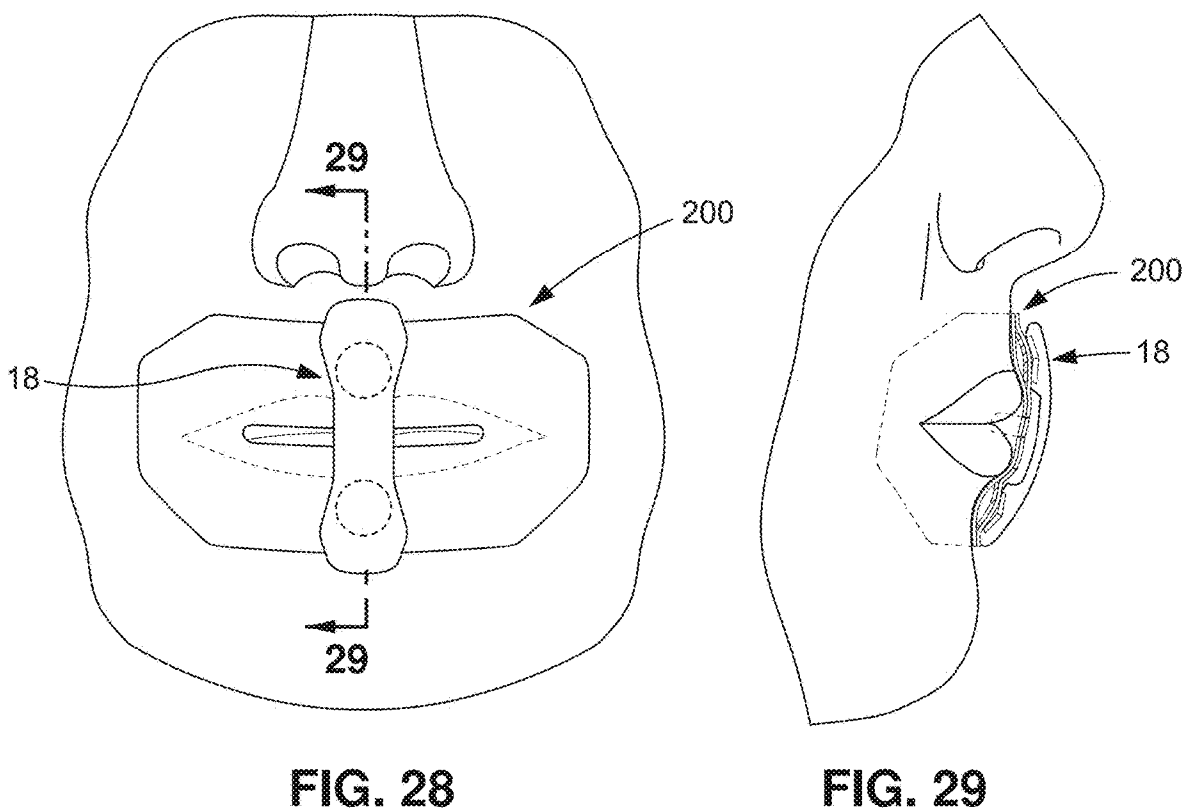
FIG. 28
FIG. 29

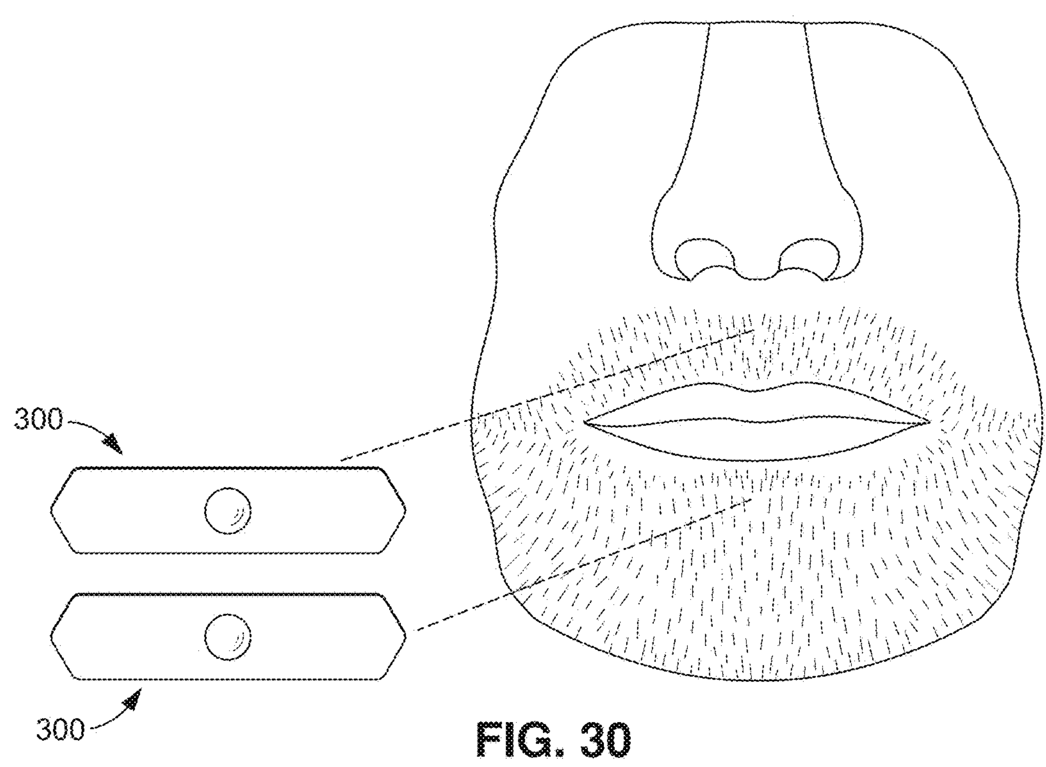
FIG. 30
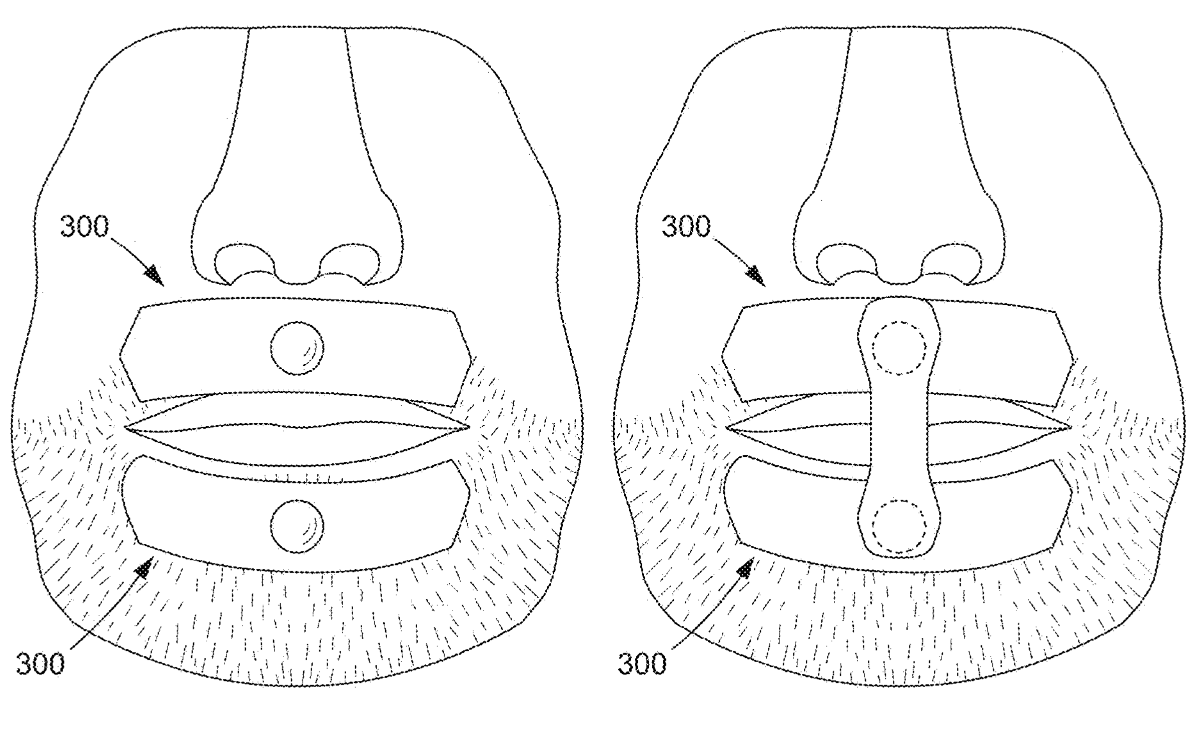
FIG. 31
FIG. 32

ANATOMICAL CLOSING SYSTEM FOR HEALTH AND WELLNESS

CROSS-REFERENCE TO RELATED APPLICATIONS

This application claims the benefit of U.S. Provisional Application Ser. No. 63/639,144, filed Apr. 26, 2024, and U.S. Provisional Application Ser. No. 63/708,683, filed Oct. 17, 2024, the contents of both of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to a system for maintaining a user's mouth in a closed position, and more particularly, to a system capable of utilizing a combination of magnetic and mechanical forces to maintain the user's mouth in the closed position.

2. Description of the Related Art

Nasal breathing has been associated with a wide variety of benefits. For instance, breathing through one's nose may facilitate filtering of dust, bacteria, viruses and other airborne particles from the inhaled air. Furthermore, the nose may include certain biological sensors that can release antimicrobial chemicals when microbes are detected in the air. Nasal breathing also helps to maintain an optimal level of moisture in the nasal lining to help clear the user's airways of inhaled particles. It is also believed that breathing through the nose may improve one's ability to exchange oxygen and carbon dioxide in one's lungs. Furthermore, breathing to a large extent through one's mouth may lead to undesirable changes in the jaw line and the teeth.

Despite the numerous advantages associated with nasal breathing, there are times when an individual may breathe through his mouth, either unknowingly, or simply by habit. For instance, when sleeping and in an unconscious state, the individual may breathe through the mouth, despite an intention to breathe primarily through the nose. The same can be said during athletic competitions, wherein the individual may have a prior intention to breathe through his nose, but may unknowingly breathe through his mouth during competition.

While there are certain products, such as tapes, that have been developed for placement over the user's mouth to keep their mouth closed to encourage breathing through the user's nose, such products are associated with certain deficiencies. For instance, if the user needs to open his mouth after the tape is placed on his mouth (such as to drink water, etc.), the user may need to remove the tape, which may be uncomfortable and may prevent the tape from being re-used.

Accordingly, there is a need in the art for an easy to use, comfortable system that helps a user maintain the user's mouth in a closed position. Various aspects of the present disclosure address this particular need, as will be discussed in more detail below.

BRIEF SUMMARY

In accordance with one embodiment of the present disclosure, there is provided a system for holding a portion of a user's body in a desired configuration. The system includes a pair of metallic elements each being configured to be attachable to the user's body at respective first and second regions of the user's body. The system additionally includes a band having a main body and at least two magnets coupled to the main body. The main body includes a middle portion and a pair of distal portions on respective sides of the middle portion. At least one of the at least two magnets is coupled to a respective one of the pair of distal portions, with each magnet being configured to be magnetically attractable to one of the pair of metallic elements. The pair of metallic elements and the band are configured to exert a force on the user's body to restrict separation of the first and second regions when the band is magnetically connected to the pair of tabs.

The main body of the band may include a plurality of teeth integral to the main body and configured to facilitate mechanical coupling with the pair of metallic elements. The plurality of teeth may include a first set of teeth positioned adjacent a first one of the at least two magnets and a second set of teeth positioned adjacent a second one of the at least two magnets. The system may additionally include a mesh material extending over the pair of metallic elements and configured to enable at least partial advancement of certain ones of the plurality of teeth therein. The system may also include a rubber material extending over the pair of metallic elements and configured to enable flexing in response to engagement with the plurality of teeth.

The band may include a pair of recesses formed in respective ones of the pair of distal portions. The at least two magnets may include a first pair of magnets in a first one of the pair of recesses and a second pair of magnets in a second one of the pair of recesses.

The pair of metallic elements may be integrated into a single tab having a first region, a second region and a slit between the first region and the second region. A first one of the pair of metallic elements may be positioned in the first region and a second one of the pair of metallic elements may be positioned in the second region. The single tab may include an adhesive to facilitate adhering of the tab to the user.

Each one of the pair of metallic elements may be integrated into a respective one of a pair of tabs, with each one of the pair of tabs having an adhesive to facilitate adhering of the tab to the user.

The pair of distal portions of the band may be moveable relative to each other to facilitate size adjustment of the band.

According to another embodiment, there is provided a method of applying a restrictive force to a user adjacent a user's mouth. The method includes adhering a pair of metallic elements on opposite sides of the user's mouth and magnetically connecting a rigid band to the pair of metallic elements to facilitate application of a force on the opposite sides of the user's mouth to restrict opening of the user's mouth.

The step of adhering the pair of metallic elements may include adhering a single tab to the user, with the single tab including the pair of metallic elements.

The step of adhering the pair of metallic elements may include adhering a pair of tabs to the user, with each of the pair of tabs including a respective one of the pair of metallic elements.

The method may additionally include the step of mechanically connecting the rigid band to the pair of metallic elements.

The step of mechanically connecting the rigid band to the pair of metallic elements may include engaging teeth on the band with a cover extending over the pair of metallic elements.

The method may also include the step of adjusting a size of the band by adjusting a distance between a pair of distal portions of the band.

According to another embodiment, there is provided a system for holding a portion of a user's body in a desired configuration. The system includes a pair of tabs, with each tab including a flexible body and a metallic element coupled to the flexible body. The flexible body includes an adhesive on a surface thereof to facilitate selective attachment of the tab to the user's body. The pair of tabs are configured to be attachable to the user's body in spaced relation to each other. The system additionally includes a band having a main body and at least two magnets coupled to the main body. The main body includes a middle portion and a pair of distal portions on respective sides of the middle portion. At least one of the at least two magnets is coupled to a respective one of the pair of distal portions, with each magnet being configured to be magnetically attractable to one of the pair of tabs to facilitate magnetic attraction. The main body and the pair of tabs are configured to be mechanically coupled to each other when the magnets of the band are magnetically coupled to the pair of tabs.

The pair of tabs may be defined by a pair of strips, each strip having an elongate linear base and a plurality of metallic elements coupled to the base in spaced relation to each other. The strips may be attachable in opposed, generally parallel relation to each other, with the metallic elements on one strip being aligned with corresponding metallic elements on the opposing strip. A plurality of bands may be coupled to the pair of strips, with each band being connected to an aligned pair of the metallic elements. The pair of strips and plurality of bands may be particularly useful in closing wounds or cuts.

The main body of the band may include a plurality of teeth configured to facilitate mechanical coupling with the pair of tabs. The flexible body may include a mesh material capable of enabling at least partial advancement of certain ones of the plurality of teeth therein.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 24 is an upper perspective view of the one-piece tab installed on the mouth of the user;

FIG. 25 is a front view of the one-piece tab installed on the mouth of the user;

FIG. 26 is a side cross sectional view of the one-piece tab installed on the mouth of the user;

FIG. 27 is an upper perspective view of the installed one-piece tab engaged with the band;

FIG. 28 is a front view of the installed one-piece tab engaged with the band;

FIG. 29 is a side cross sectional view of the installed one-piece tab engaged with the band;

FIG. 30 is a front view depicting a pair of tabs configured for use on a user with facial hair;

FIG. 31 is a front view depicting the pair of tabs of FIG. 29 installed on the user; and FIG. 32 is a front view of the pair of installed tabs engaged with a band.

Common reference numerals are used throughout the drawings and the detailed description to indicate the same elements.

DETAILED DESCRIPTION

Figure 1:
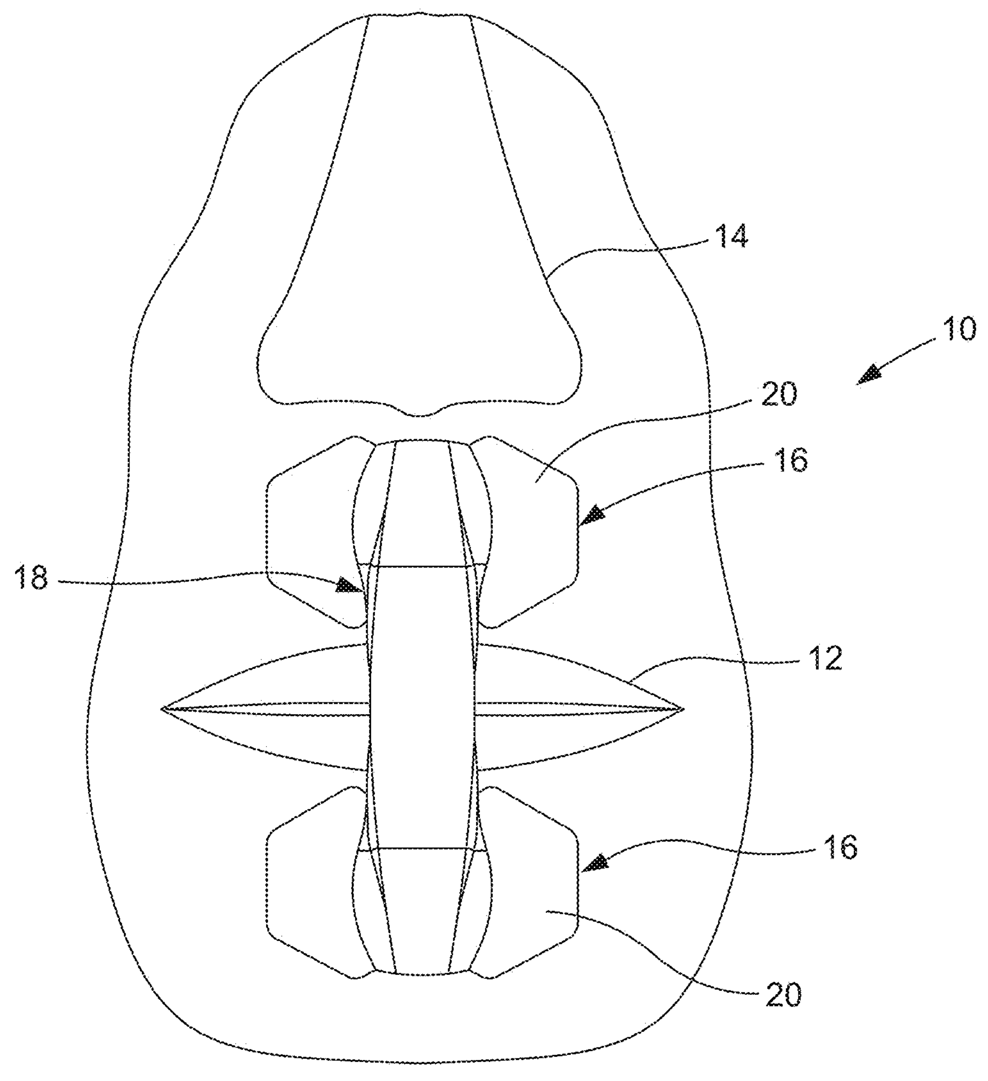
FIG. 1 is a front view of a mouth closing system depicted in use on a face of a user.

The detailed description set forth below in connection with the appended drawings is intended as a description of certain embodiments of a mouth closing system and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Referring now to the drawings wherein the showings are for purposes of illustrating preferred embodiments of the present disclosure, and are not for purposes of limiting the same, there is depicted a system 10 designed to restrict opening of a user's mouth 12 in order to encourage breathing through the user's nose 14. There are believed to be several benefits associated with breathing through one's nose 14, such as filtering out foreign particles, warming and moisturizing inhaled air, and releasing nitric oxide (NO), which is a vasodilator to improve oxygen circulation in the body. Along these lines, breathing primarily through one's mouth 12 may be associated with several health risks, including inhaling unfiltered air, allergic reactions to allergens, asthma, bad breath, tooth decay, gum inflammation, snoring, sleep apnea, as well as teeth or jaw abnormalities, such as undesired changes in the jaw or teeth structure. Thus, use of the system 10 described herein to restrict breathing through one's mouth to encourage breathing through one's nose may yield several health benefits, while helping to avoid several health risks.

Figures 2, 3:
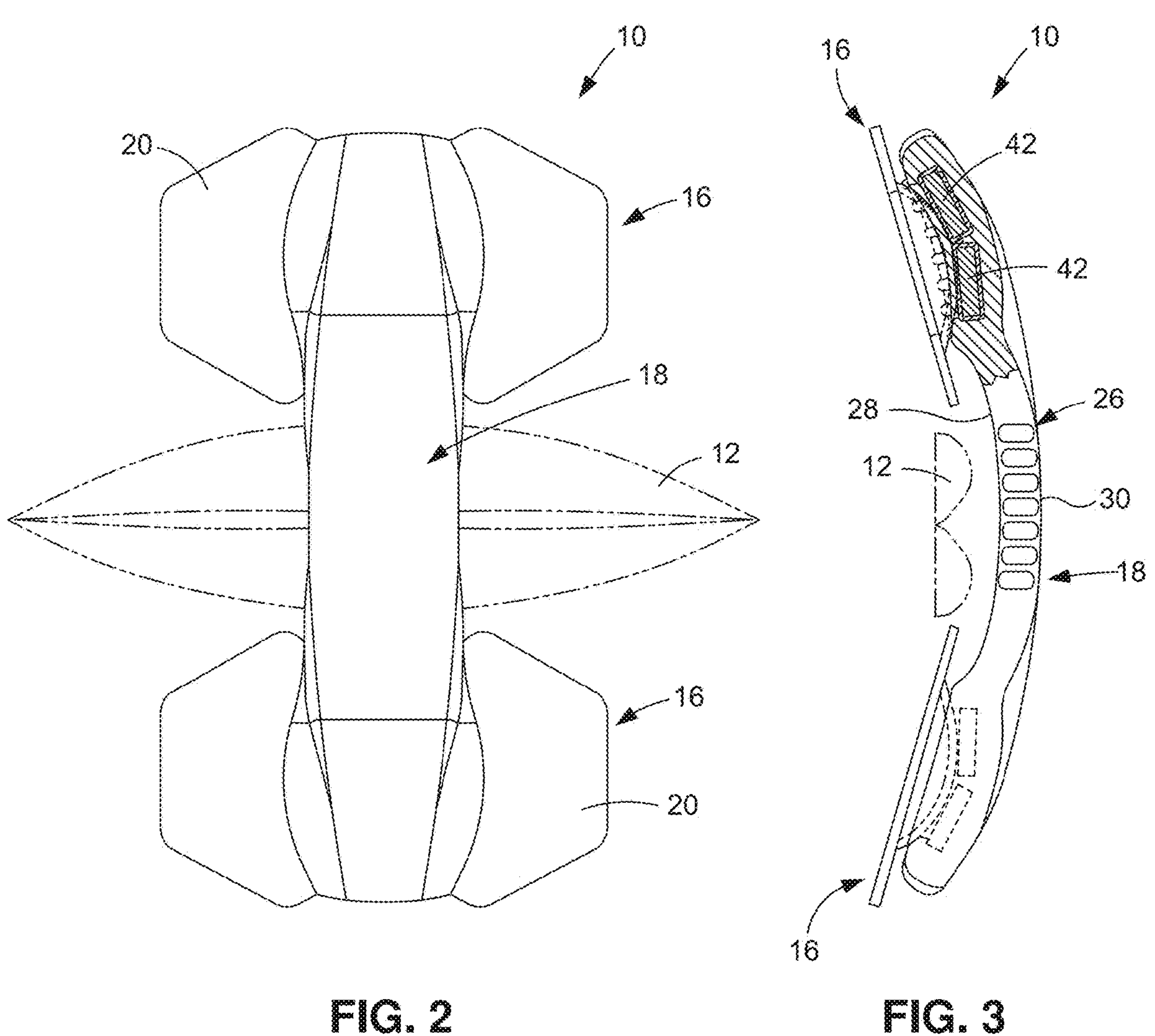
FIG. 2 is an enlarged view mouth closing system depicted in FIG. 1.
FIG. 3 is a side view of the mouth closing system of FIG. 1.
Figure 4:
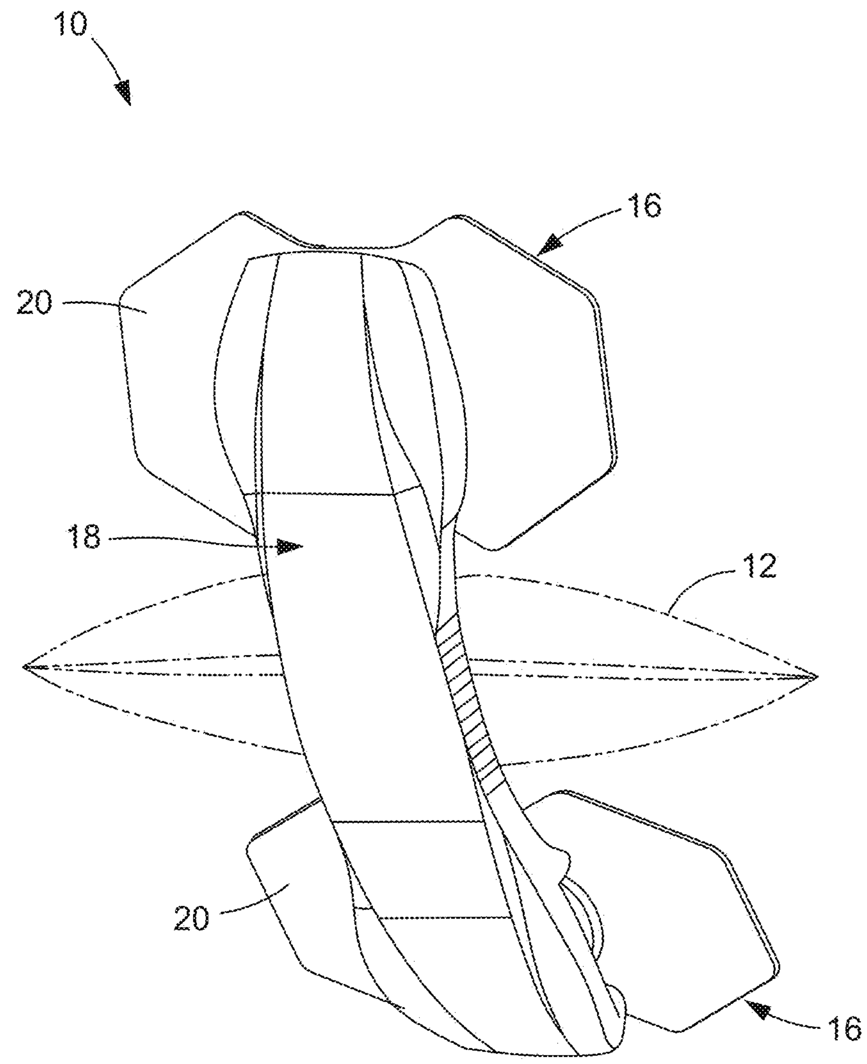
FIG. 4 is a perspective view of the mouth closing system of FIG. 1.
Figure 5:
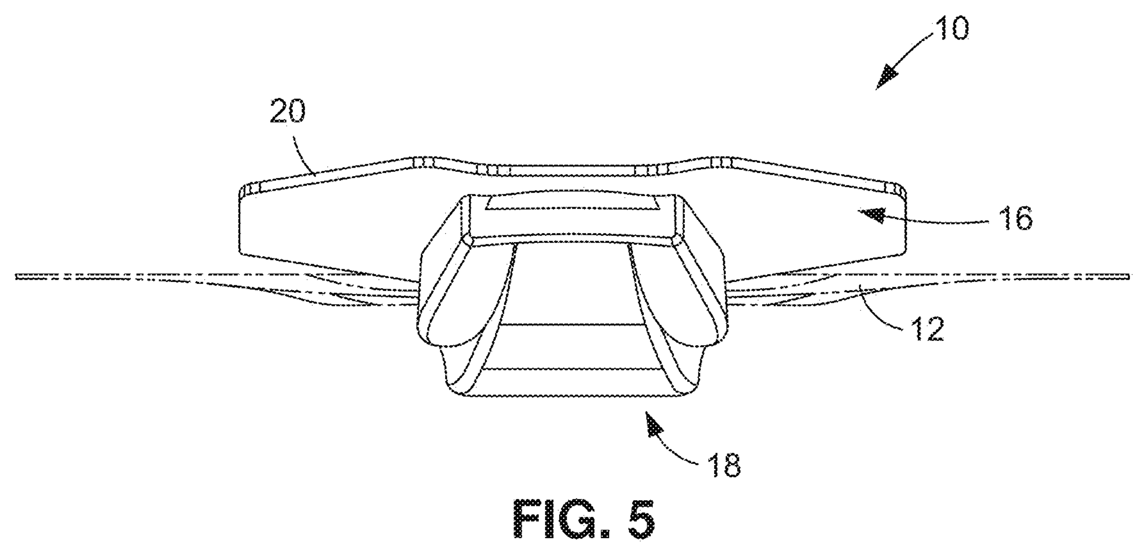
FIG. 5 is a top view of the mouth closing system of FIG. 1.
Figure 6:
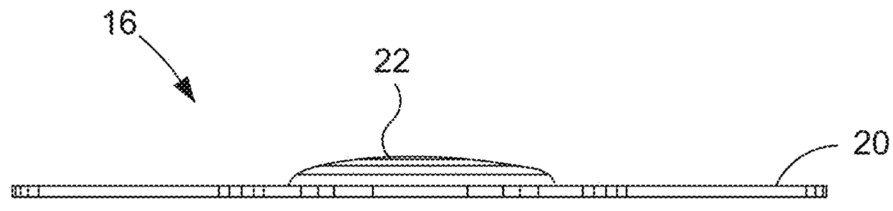
FIG. 6 is a side view of an applique that is part of the mouth closing system of FIG. 1.

In more detail, the system 10 generally includes a pair of adhesive tabs (e.g., appliques, stickers, etc.) 16 and a band 18 that is operatively connectable to the pair of adhesive tabs 16. FIG. 1 is a front view of the system 10 shown on a user, with a first tab 16 adhered to the user above the user's lip and a second tab 16 adhered to the user below the user's lips, and the band 18 extending across the user's lips from the first tab 16 to the second tab 16. FIG. 2 is an enlarged front view of the system 10, FIG. 3 is an enlarged side view of the system 10, FIG. 4 is an upper perspective view of the system 10, and FIG. 5 is a top view of the system 10.

Each tab 16 may include including a flexible body 20 and the metallic element 22 coupled to the flexible body 20. The flexible body 20 is configured to be attached directly to the user's skin, either above an upper lip, between the upper lip and the user's nose, or below a lower lip, between the lower lip and the user's chin. The flexible body 20 may be capable of bending/flexing to conform to the unique anatomy of the user's facial structure. According to one embodiment, the flexible body 20 includes an adhesive disposed on an outer surface thereof to enable selective attachment of the tab 16 to the user. A peel-away layer may be coupled to the flexible body 20 and cover the adhesive to preserve the adhesive until the tab 16 is to be used.

Figure 7:
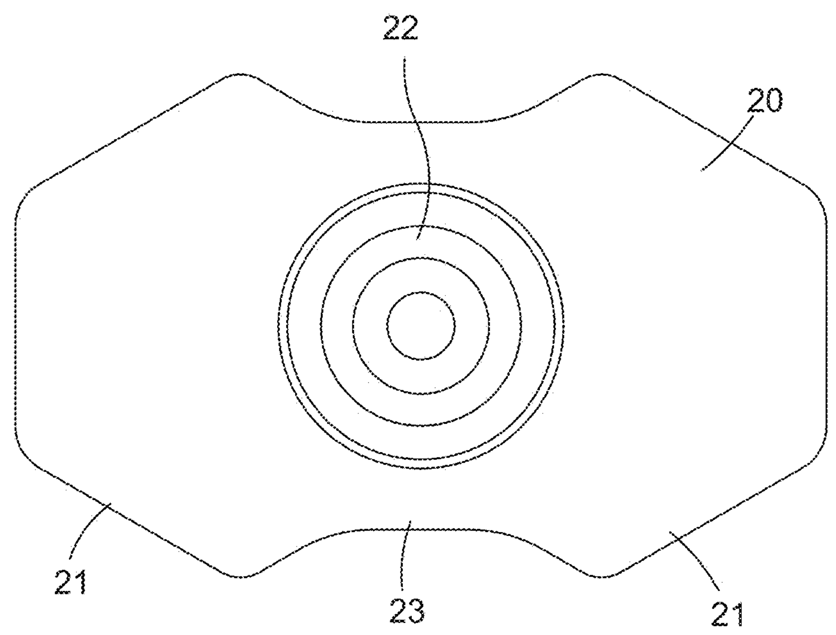
FIG. 7 is a top view of the applique of FIG. 6.

According to one embodiment, and when viewed in from the perspective depicted in FIG. 7, the flexible body 20 defines outer periphery including a pair of enlarged end portions 21 separated by a narrow middle portion 23. The tab 16 shown in FIG. 7 is designed to be used on either side of the mouth 12. It is contemplated that the configuration of the tab 16 may vary from that illustrated in the Figures without departing from the spirit and scope of the present disclosure.

According to one embodiment, the flexible body 20 is a composite structure including a pair of outer layers with the metallic element 22 being captured between the outer layers. The layers may be secured to each other via adhesive, lamination, or other means known in the art. The metallic element 22 is configured to interact with one or more magnets coupled to the band 18 when the band 18 is positioned adjacent the mouth 12 and the flexible body 20 is attached to the user. The metallic element 22 is positioned such that at least a portion of the flexible body 20 extends radially outward beyond the metallic element 22 to define a flexible peripheral portion. While the present disclosure describes the magnet as being part of the band 18 and the metallic element 22 as being part of the tab 16, it is contemplated that the configuration may be reversed without departing from the spirit and scope of the present disclosure. That is, the magnet may be part of the tab 16 and the metallic element 22 may be part of the band 18. Furthermore, although the present disclosure describes the metallic element 22 as being captured between two layers (e.g., an inner layer and an outer layer) of the flexible body 20, it is contemplated that in certain embodiments, the metallic element 22 may be secured to only one layer, and thus, may be exposed. For instance, the metallic element 22 may be secured to an inside of a single layer to be captured between that layer and the user's skin when the tab 16 is attached to the user. Alternatively, the metallic element 22 may be secured to an outside of the single layer to be exposed and extend on an outer surface of the flexible body 20 when the tab 16 is attached to the user.

According to one embodiment, the metallic element 22 includes a convex surface defining a "domed" or arcuate configuration to enhance magnetic engagement with the remotely located magnet. In this regard, flat-to-flat attachment between the magnet and the metallic element 22 may create uncomfortable torque on the user's skin. Thus, by creating a domed engagement surface on the metallic element 22, such uncomfortable torque may be avoided. Furthermore, the convex surface defines a suitable structure which does not inhibit motion of the magnet thereover, and instead, allows the magnet to move or float along during engagement between the tab 16 and the magnet. In particular, the magnet may move along at least one axis, and more preferably along at least two axes, relative to the metallic element 22 while the metallic element 22 remains magnetically engaged with the magnet.

While the foregoing describes the metallic element 22 as having a convex surface that interfaces with the magnet, it is contemplated that other embodiments of the metallic element 22 may have a flat surface that interfaces with the magnet. In this respect, the scope of the present disclosure is intended to encompass any variation of metallic element 22 and magnet, where one or both of the metallic element 22 and magnet may have convex surfaces, or flat surfaces, or in some cases, neither the metallic element 22.

The domed or arcuate surface may be positioned opposite a generally planar surface of the flexible body 20. It is understood that the outer periphery of the metallic element 22 may be any shape, including circular, oval, quadrangular, etc. The advantages of the convex engagement between the metallic element 22 and the corresponding magnet may also be effectuated through the use of an arcuate or dome shaped magnet. In this respect, the metallic element 22 and/or the magnet may have an arcuate or rounded surface.

According to one embodiment, the flexible body 20 includes at least one perforation (not shown) extending through the flexible body 20 to ventilate the user's skin residing under the tab 16 to prevent sweat from building up under the tab 16. A long these lines, a buildup of sweat between the tab 16 and the user's skin could diminish the ability of the adhesive to effectively secure the tab 16 to the user's skin. Thus, by incorporating the perforation(s), the sweat can evaporate or flow away from the user's skin to more effectively maintain adhesion between the tab 16 and the user's skin.

In one implementation, at least one layer of the flexible body 20 may be formed from a woven material or mesh material. The woven or mesh material may facilitate mechanical interaction with the band 18, as will be described in more detail below.

For more information regarding tabs 16, please refer to U.S. Pat. No. 10,556,095, entitled GOGGLE BREATHING SYSTEM, U.S. Pat. No. 9,510,969, entitled NASAL ELEMENT FOR A BREATHING SYSTEM, U.S. Pat. No. 9,283,106, entitled BREATHING SYSTEM, U.S. Pat. No. 9,675,493, entitled GOGGLE BREATHING SYSTEM, the contents of each of which being expressly incorporated herein by reference.

The band 18 includes an arcuate main body 26 having a concave inner surface 28 and an opposing convex outer surface 30. The main body 26 includes a middle portion 32 defining an apex which is located between two distal portions 34, wherein each distal portion terminates 34 at a respective distal tip 36. The two distal tips 36 are spaced from each other by a distance, $D_1$ (e.g., a band length) which allows the band 18 to fit over the user's mouth 12, with the distal portions 34 being positioned adjacent opposing regions of the user's mouth 12. The band 18 may be fabricated in various sizes to accommodate differently sized mouths. A long these lines, the distance $D_1$ may be anywhere from 1.0 inch for use on a small mouth (e.g., for a child), to over 2.5 for use on a larger mouths. For an average mouth, the distance $D_1$ may be approximately equal to 1.75 inches. Furthermore, the degree of curvature of the band 18 may vary to accommodate different lip anatomy. As will be discussed in more detail below, certain embodiments of the band 18 may be configured to enable adjustment in the magnitude of distance $D_1$.

The main body 26 includes a pair of opposed longitudinal edges 38 and a pair of opposed transverse edges 40, which essentially define the aforementioned distal tips 36. The distance between the opposed longitudinal edges 38 defines a band thickness which may vary along the length of the band 18 (e.g., between the distal tips 36).

According to one embodiment, the main body 26 is rigidly formed so as to substantially maintain its shape. Along these lines, the main body 26 is preferably more resistant to bending, or flexing than is the skin of the user. In this respect, the main body 26 is capable of being disposable in compression, that is to say, the main body 26 is capable of having a force applied thereto. The main body 26 may be formed of plastic, rubber, metal, wood, fiberglass, or other materials known in the art. It is contemplated that the main body 26 may be molded, printed, or formed via other techniques known by those skilled in the art. In one particular embodiment, the main body 26 may include a plastic core with a silicone outer layer.

Figure 8:
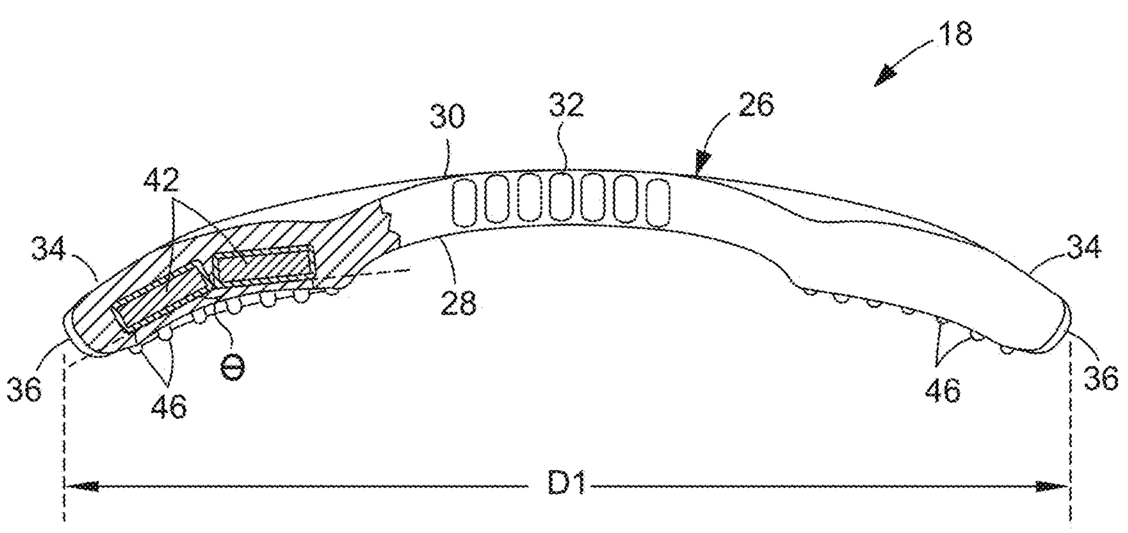
FIG. 8 is a side view of a band that is part of the mouth closing system of FIG. 1.
Figure 9:
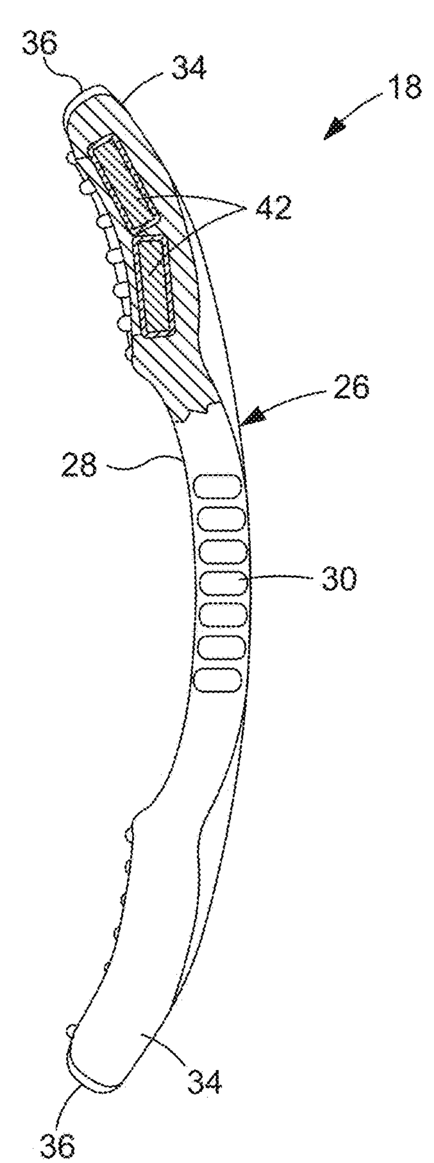
FIG. 9 is another side view of the band of FIG. 8.
Figure 10:
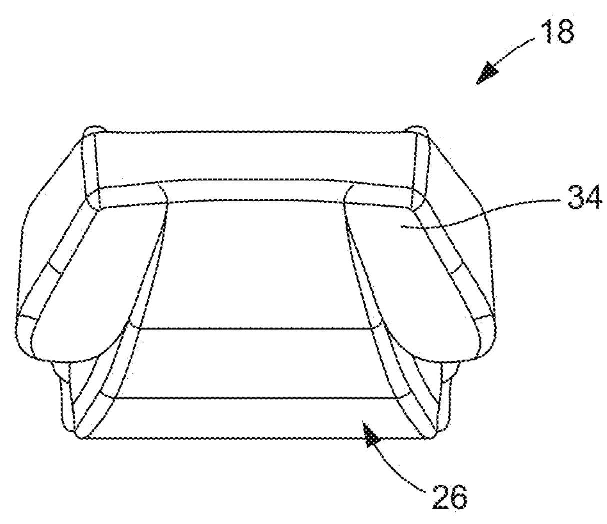
FIG. 10 is a top view of the band of FIG. 8.
Figure 11:
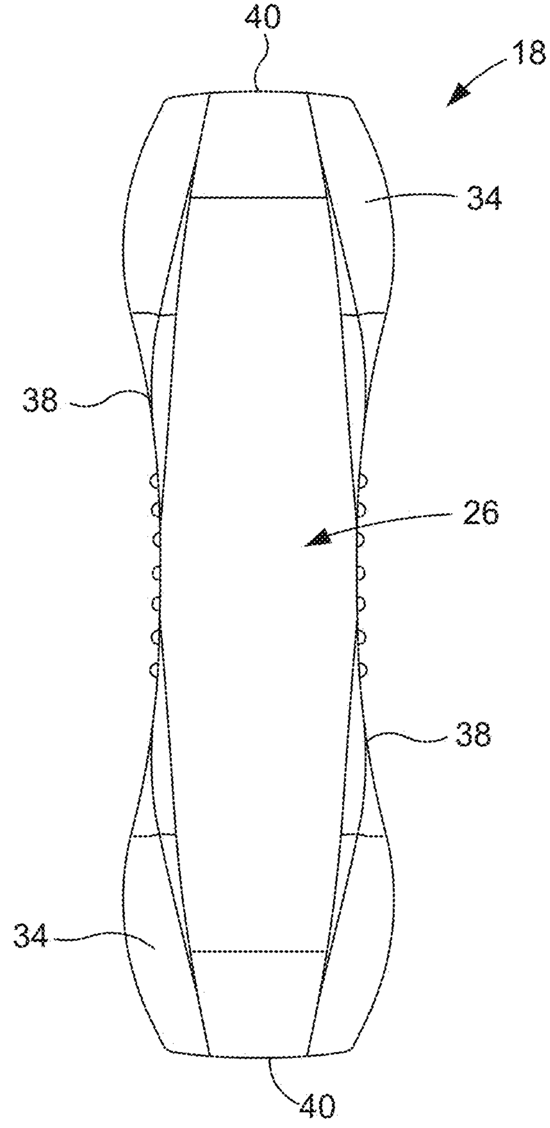
FIG. 11 is a front view of the band of FIG. 8.

The band 18 further includes a plurality of magnets 42 adjacent the distal portions 34 of the main body 26. In the exemplary embodiment, the band 18 includes a pair of magnets 42 at each distal portion 34. The magnets 42 in a given distal portion of the band 18 may be angularly offset from each other, such that an exposed surface of one magnet 42 may be arranged in a non-planar orientation relative to the exposed surface of the adjacent magnet 42. FIG. 8 shows plane 43 being parallel to exposed surface 42*a* of a first magnet 42, which plane 45 is parallel to exposed surface 42*b* of second magnet 42. The angle Θ between the planes 43, 45 may be between 125-179 degrees. This configuration may allow the pair of magnets 42 to define a slightly concave configuration, or A-frame configuration. Such a configuration may allow the magnets 42 to more effectively magnetically interface with the metallic element 22 in the tab 16.

The magnets 42 may be received within a cavity or recess 44 formed within the main body 26 that is substantially complementary in shape and size to the pair of magnets 42. According to one embodiment, the main body of the band 18 may be molded around the magnets 42 to secure the magnets 42 therein. The magnets 42 may be adhered or otherwise coupled to the main body 26 using fastening mechanisms known by those skilled in the art.

According to one embodiment, the band 18 may include a plurality of teeth 46 formed at each distal portion 34. The teeth 46 are configured to grip into an interface portion of the flexible body 20 to strengthen the connection between the band 18 and the tabs 16. The interface portion may include a woven surface adapted to enable penetration of the teeth 46 through the woven surface to facilitate connection between the band 18 and the tabs 16. Alternatively, the interface portion may include a rubber surface when engaged with the teeth 46. The flexion/distortion of the rubber surface around the teeth 46 may enhance grip/friction between the teeth 46 and the rubber surface to strengthen the connection between the band 18 and the tabs 16. In this regard, the band 18 and tabs 16 may be coupled via a combination of magnetic force, as well as mechanical force via interaction between the teeth 46 and flexible body 20. The main body of the band 18 and the tabs 16 may thus be mechanically coupled to each other so as to mechanically resist shear movement of the band 18 relative to the tabs 16. The engagement between the flexible body 20 and the teeth 46 may be particularly suitable for resisting shear forces; that is resisting forces that are in a direction tangent to an outer surface of the tab 16.

The teeth 46 may extend away from an inner surface of the distal portion 34, in a direction away from the magnets 42. The teeth 46 may be tapered in configuration, with a cross-sectional area of each tooth 46 decreasing as the tooth 46 extends away from the distal portion 34. In this regard, a maximum cross-sectional area of each tooth 46 may be defined where the tooth 46 extends from the distal portion 34, and a minimum cross-sectional area of each tooth 46 may be defined by an end of the tooth 46 positioned away from the distal portion 34 of the band 16.

Figure 12:
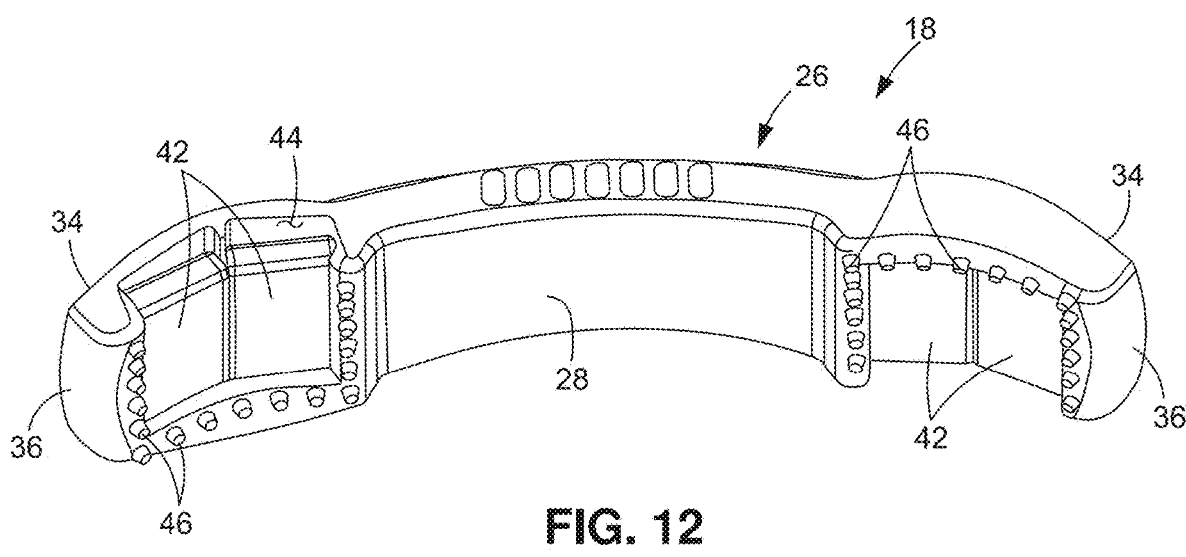
FIG. 12 is a perspective view of the band of FIG. 8.
Figure 13:
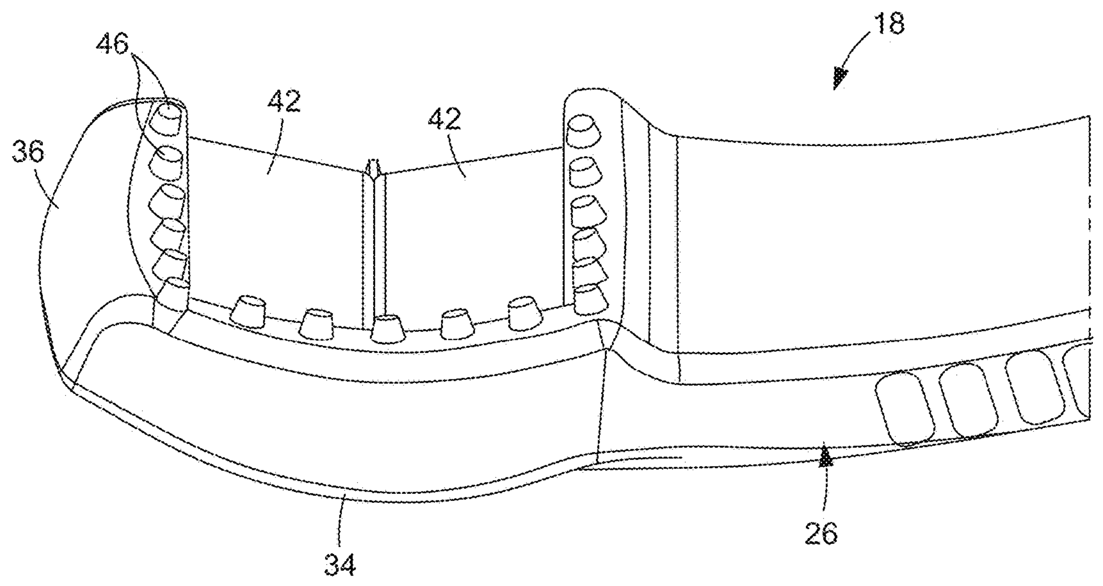
FIG. 13 is an enlarged perspective view depicting one end portion of the band of FIG. 8.

The teeth 46 may be positioned around the magnets 42. In the embodiment depicted in FIGS. 12 and 13, the teeth 46 extend around three sides of the pair of magnets 42, with the remaining fourth side being formed without teeth 46. Instead, the fourth side is configured to facilitate slidable insertion of the magnets 42 into the band 18 during assembly of the band 18. The side formed without teeth 46 may be on one side of the band 18 at one distal portion 34, and an opposite side of the band 18 at the other distal portion 34.

Figure 14:
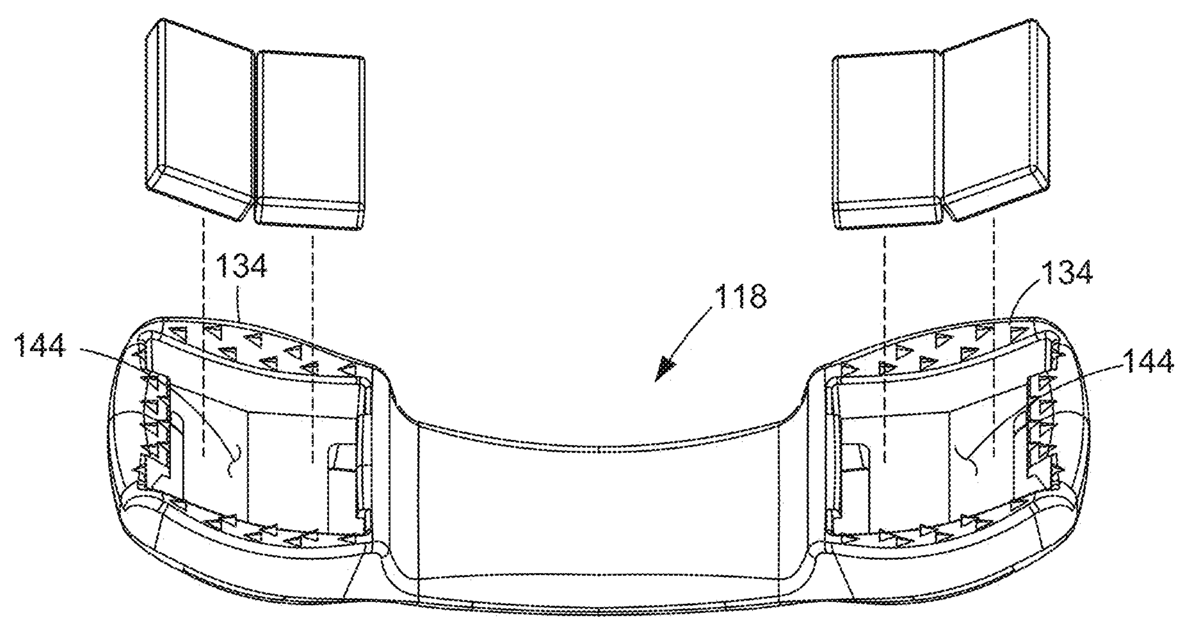
FIG. 14 is a perspective view of another embodiment of the band configured to facilitate snap-engagement with a pair of magnets at each end portion of the band.
Figure 15:
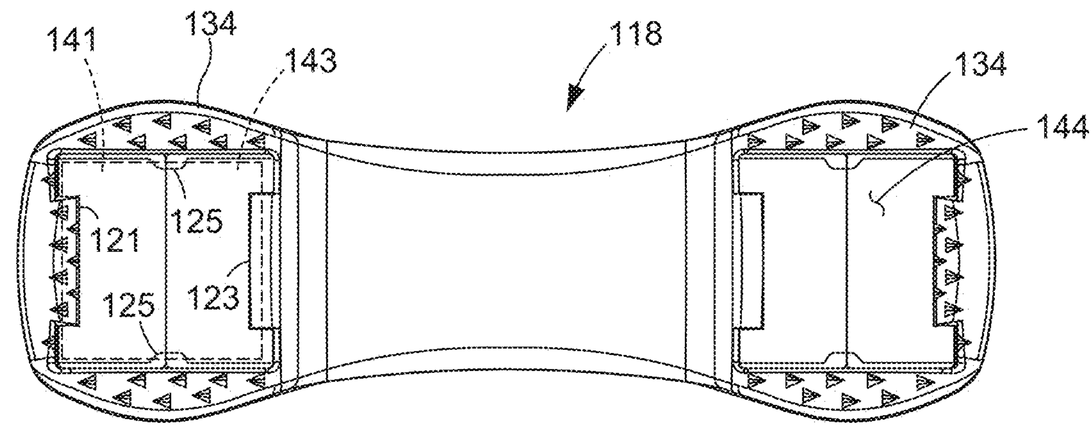
FIG. 15 is a bottom view of the band depicted in FIG. 14.

Although the exemplary embodiment shows the teeth 46 only on three sides of the pair of magnets 42, it is contemplated that the teeth 46 may completely surround the pair of magnets 42, particularly when the magnets 42 are snapped into place on the band 18 and the fourth side is not needed for sliding the magnets 42 into the band 18. FIGS. 14 and 15 depict an embodiment of the band 118 adapted for snap engagement with a pair of magnets at each distal portion 134 of the band 118. In this regard, each distal portion 134 includes a cavity or recess 144 sized to receive the magnets, and several flanges configured to retain the magnets within the recess 144. The flanges may include a lateral flange 121, a medial flange 123 and a pair of side flanges 125. The flanges 121, 123, 125 may extend over the magnets after the magnets are snapped into the recess 144. In more detail, FIG. 15 depicts dashed lines representative of a pair of magnets 141, 143 received within a recess 144. During installation, a first one of the pair of magnets 141 may be placed under lateral flange 121 with the other end of the magnet (i.e., the end opposite the lateral flange) 141, resting on top of the side flanges 125. The second one of the pair of magnets 143 may be placed under medial flange 123 with the other end of the magnet (i.e., the end opposite the medial flange) 123 resting on top of the side flanges 125. A force may be applied to the ends of the magnets 141, 143 resting on the side flanges 125 to cause the magnets 141, 143 to snap into place, such that the ends of the magnets 141, 143 that were previously resting on top of the side flanges 125 are now captured within the recess 144 by the side flanges 125, along with the lateral flange 121 (in the case of magnet 141) and medial flange 123 (in the case of magnet 143).

During use, the system 10 may be specifically configured to be selectively transition between an ON configuration, wherein the system 10 may inhibit opening of a user's mouth 12, and an OFF configuration, wherein the system 10 may not inhibit opening of the user's mouth 12, despite part of the system 10 remaining adhered to the user. Thus, if the user wants to open their mouth 12 for talking, drinking, etc., the entire system 10 may not require removal from the user's body. In particular, the tabs 16 may remain adhered to the user, while the band 18 may be removed to allow for opening of the user's mouth 12. When the system 10 is in the ON configuration, the band 18 may be coupled to the tabs 16 via a combination of at least two forces: 1) a magnetic force, and 2) a mechanical force. The magnetic force refers to the force between the magnets 42 and the metallic element 22. The mechanical force refers to the engagement or mating between the teeth 46 and the interface portion of the flexible body 20, e.g., the mesh/woven material of the flexible body 20 or rubber surface of flexible body 20. In this regard, the interaction between the teeth 46 and the interface portion inhibits movement of the teeth 46 in a direction perpendicular to the axis along which a given tooth 46 extends. Thus, when the teeth 46 "bite" into interface portion, the teeth 46 may temporarily take hold in the material to restrict side-to-side movement of the teeth 46 relative to the flexible body 20. However, the band 18 may be disengaged from the tabs 16 by pulling away from the tabs 16 in a directly generally perpendicular to the flexible body 20.

Figure 16A:
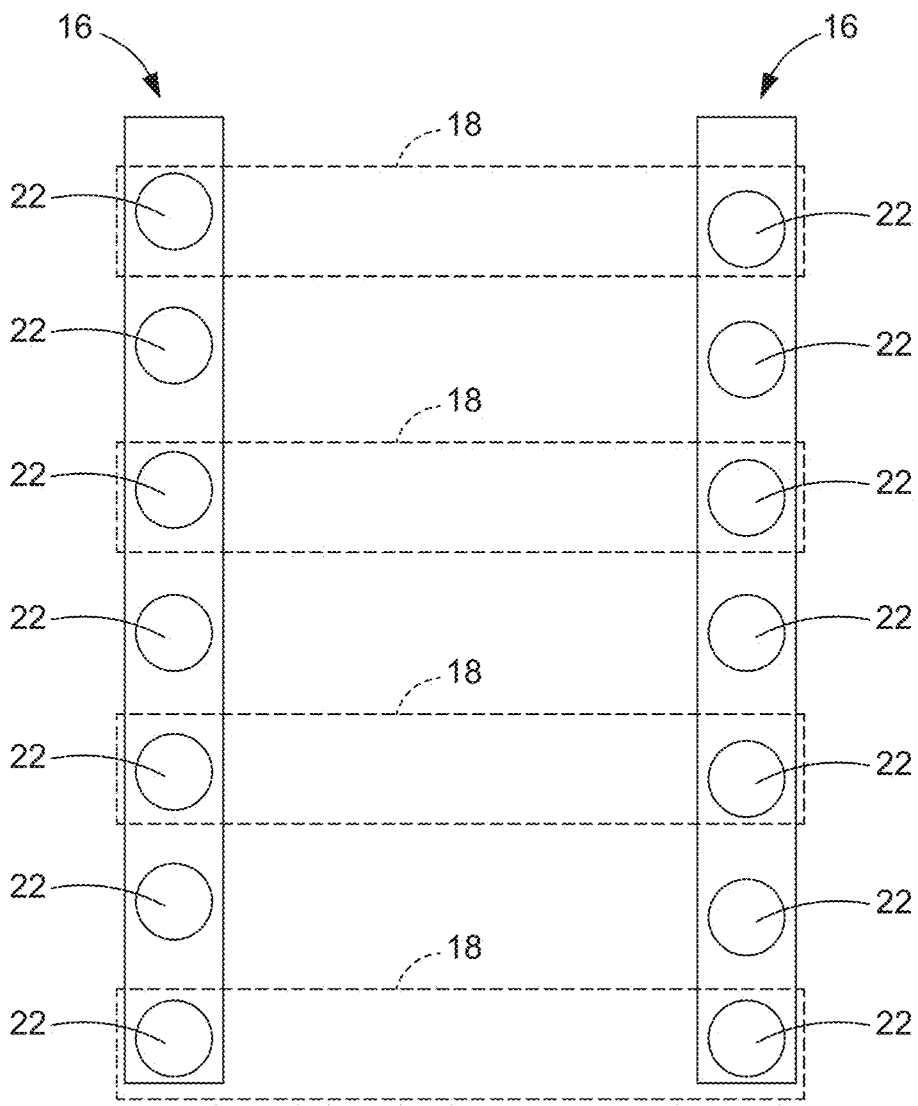
FIG. 16A is an embodiment of an anatomical closing device having a series of bands each being independently adjustable in length.

Although the foregoing use of the system is described for its use in helping a user maintain a closed mouth, it is contemplated that various implementations of the system may be used for other purposes. For instance, one embodiment of the system 10 may be particularly adapted for use in helping to close a wound. In this regard, the tabs 16 may be placed on opposite sides of the wound, and while the wound is held closed, the band 18 may be placed on the tabs 16 to prevent the wound from opening. FIG. 16A is a schematic depiction of a pair of tabs 16, each of which is elongate in configuration and includes a plurality of metallic elements coupled thereto. The tabs 16 are arranged opposite each other (on opposite sides of a wound), to enable several bands 18 to be connected to the tabs 16 to hold the tabs 16 in close proximity to each other to close the wound.

It is also contemplated that the band 18 may be configured to facilitate selective size adjustment (e.g., adjustment of distance $D_1$, in other words, adjustment of a band length), wherein the distal portions 34 may be moveable relative to each other. In this regard, the distal portions may be separate bodies/elements/structures that are connectable by zip ties or other adjustment mechanism(s) that allow for selective adjustment in the distance between the distal portions 34. Thus, once the band 18 is connected to the tabs 16, the zip ties may be pulled to move the distal portions 34 closer together, and apply a closing force on the wound to help close the wound and protect against infection, while also helping the wound to heal faster. It is also contemplated that the adjustment in the size of the band 18 may be facilitated through a telescopic band configuration, wherein different segments or sections of the band may be moveable relative to each other. The telescopic configuration may allow the band to flex (e.g., change the degree or curve and/or change the length) as may be needed to enable comfortable wearing by the user. In some cases, the size adjustment may allow for approximately ⅛ of an inch in length adjustment, although, in other embodiments, length adjustment of less than ⅛ of an inch or more than ⅛ of an inch (e.g., ¼ of an inch) may be possible without departing from the spirit and scope of the present disclosure.

Figure 16B:
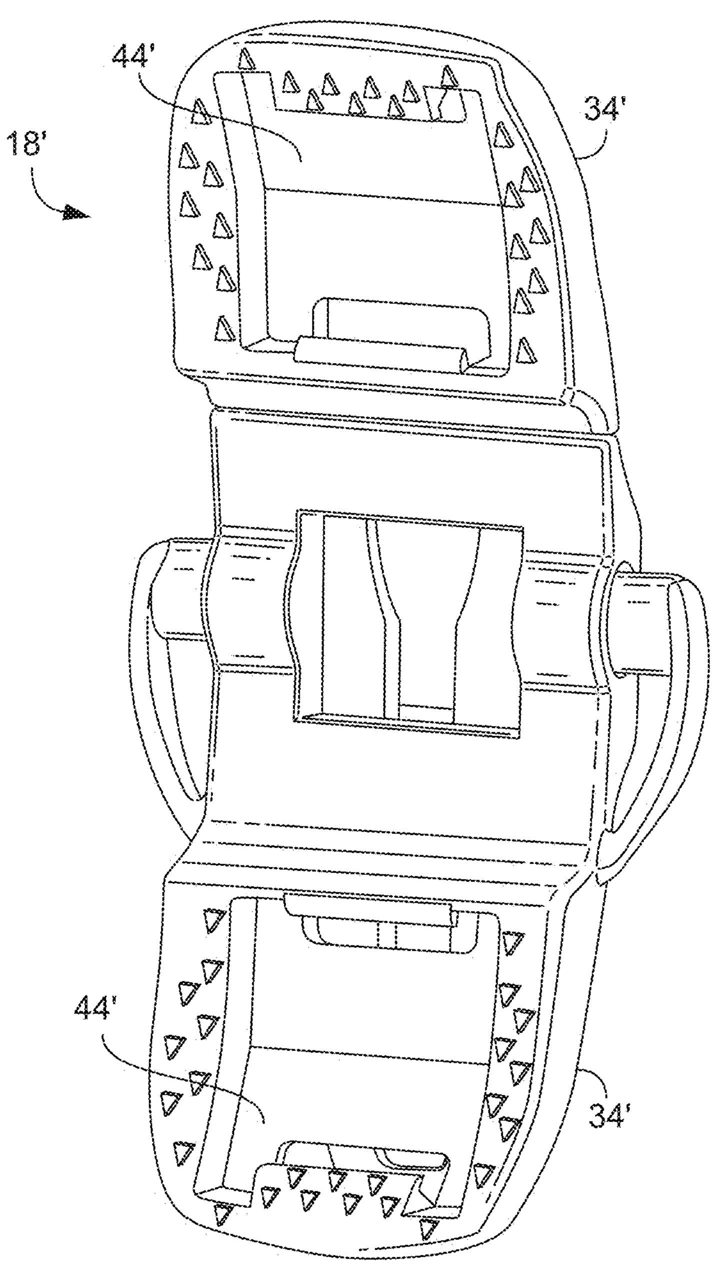
FIG. 16B is a lower perspective view of another embodiment of an anatomical closing device/band having adjustable distal portions.

FIG. 16B shows an embodiment of a band 18' having a pair of distal portions 34' that are moveable relative to each other. Each distal portion may include a cavity 44' designed to receive one or more magnets, as described in more detail above. The distal portions 34' may be configured to enable selective positional adjustment of one distal portion 34' relative to another distal portion 34' to facilitate anatomical closing or tightening, as described in more detail above. In this regard, the ability of the distal portions 34 to magnetically and mechanically engage with respective tabs 16 not only allows for anatomical restriction/closing, while the ability to adjust the position of one distal portion 34' relative to the other distal portion 34' allows the band 18' to move with the underlying anatomical structure until the anatomical structure assumes a desired position. For instance, the distal portions 34' may be placed on opposite sides of an open wound and then moved towards each other until the wound is sufficiently closed. The distal portions 34' are further configured to remain in a desired position to hold the anatomical structure in a desired position while the band 18' is engaged with the tabs 16.

Figure 16C:
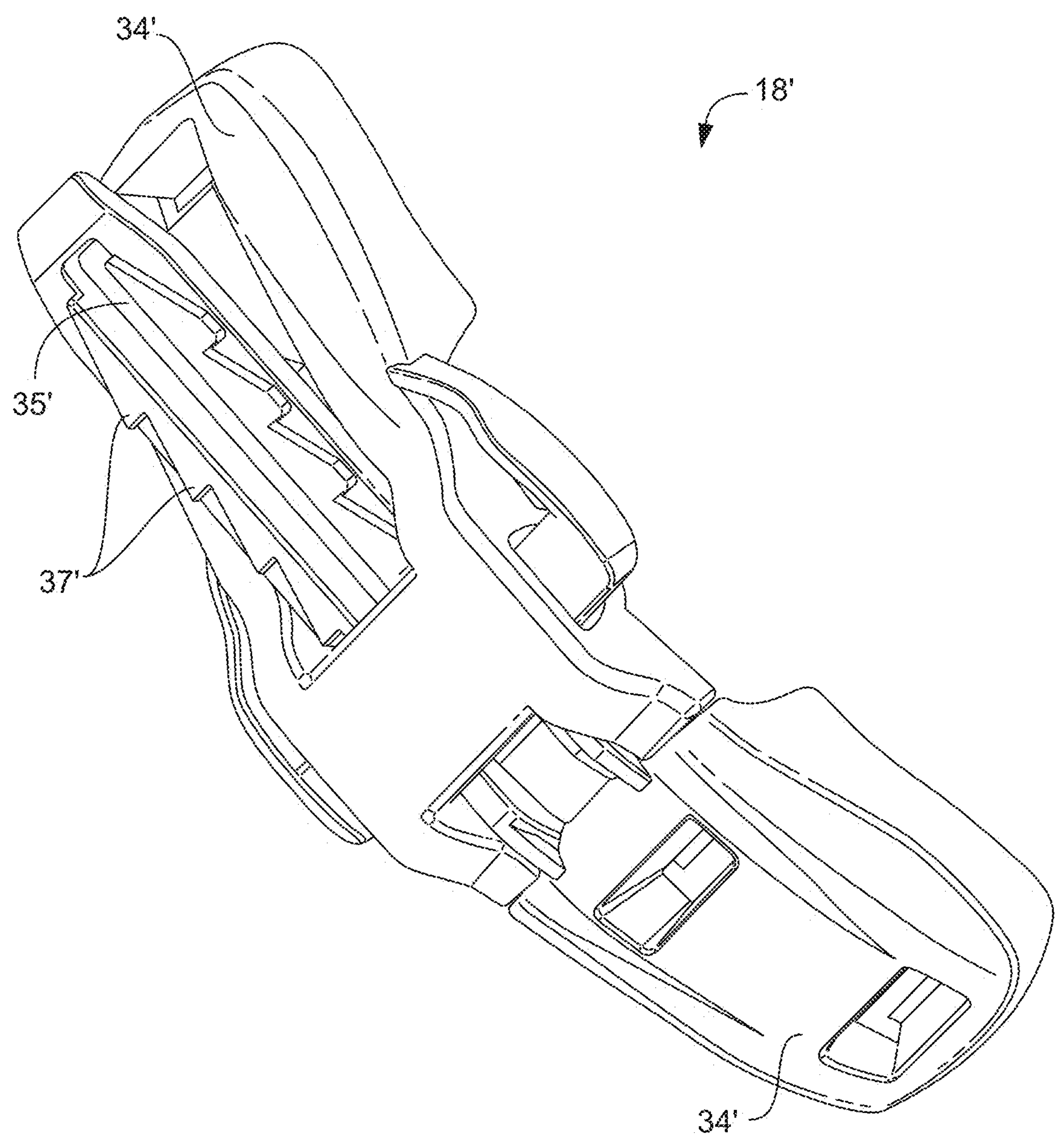
FIG. 16C is an upper perspective view of the anatomical closing device of FIG. 16B.
Figure 16D:
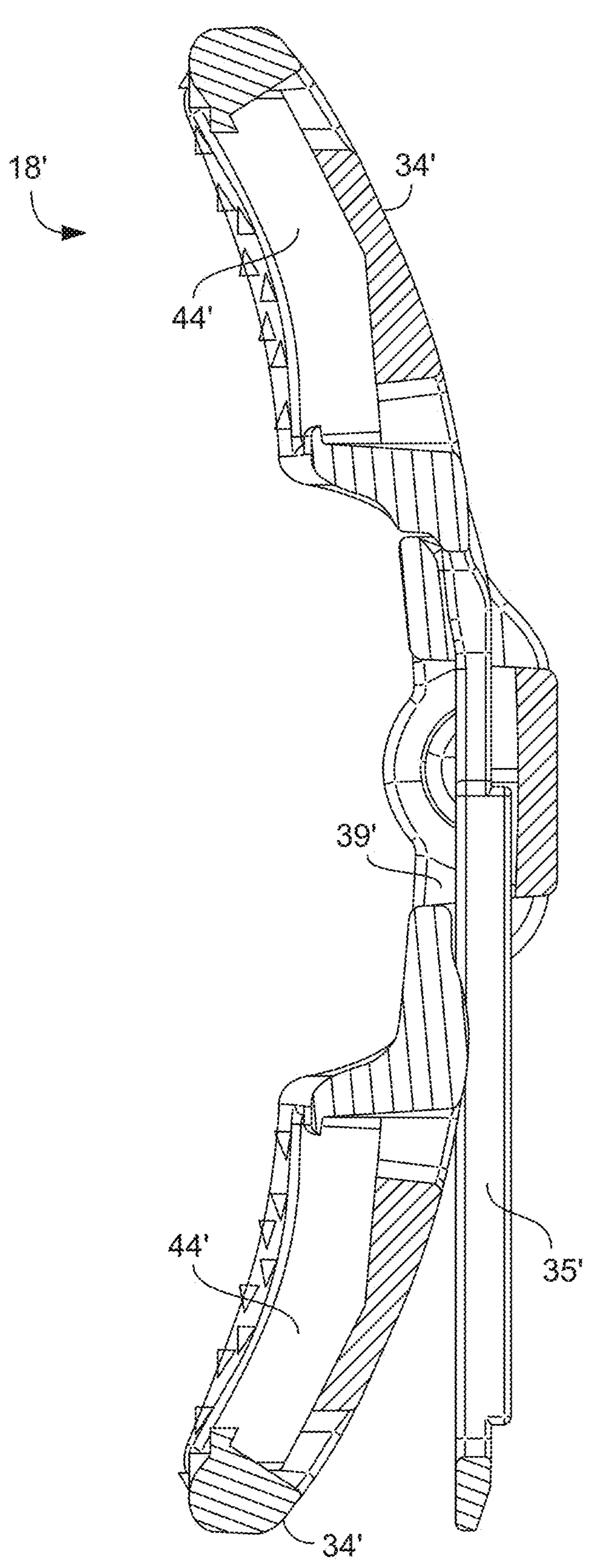
FIG. 16D is a side cross sectional view of the anatomical closing device of FIG. 16B.

According to one embodiment, the movement of the distal portions 34' is facilitated through an interconnection similar to a zip-tie. In this regard, one distal portion 34' may be coupled to an elongate strip 35' having teeth 37' formed thereon, while the other distal portion 34' may be coupled to a receptacle having a passage or opening 39' through which the elongate strip 35' may pass. The passage 39' may include a tooth or other structure that can engage with the teeth 37' on the elongate strip 35'. In particular, the tooth or other structure may allow for movement of the strip through the passage in a first direction, but restrict movement of the strip through the passage in an opposing second direction. In this regard, the distal portions 34' may initially start at a maximally spaced distance from each other, with the elongate strip 35' being connected to the passage 39' and may be moved closer to each other until the distal portions 34' assume an abutting position or a minimally spaced distance from each other. In the embodiment depicted in FIGS. 16B-16D, the distal end portions 34' are in the abutting position, having already transitioned from the maximally spaced distance from each other.

Figure 17A:
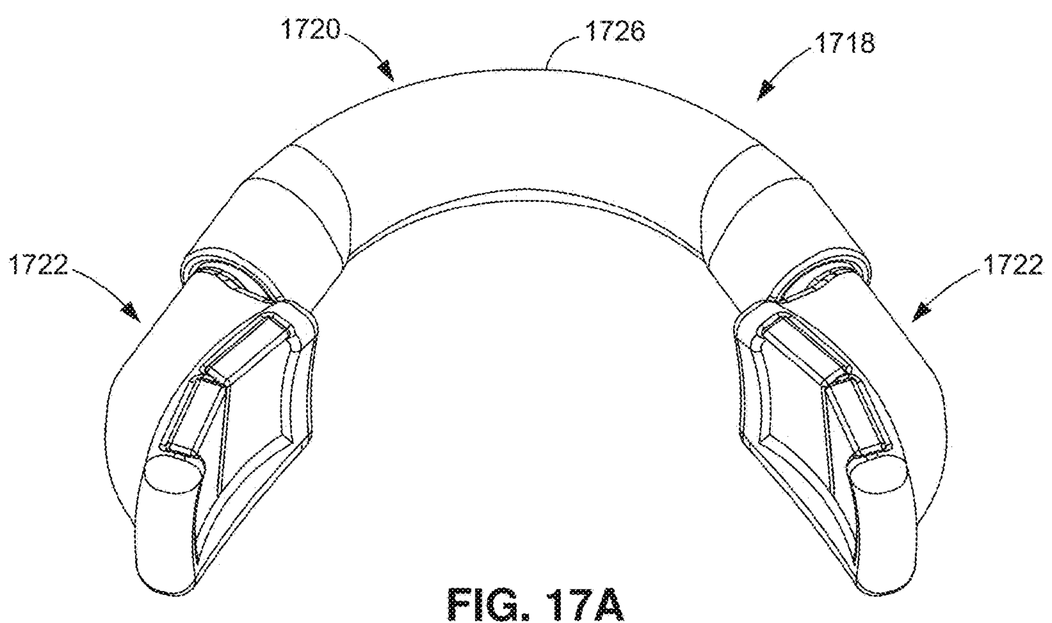
FIG. 17A is a lower perspective view of an embodiment of an adjustable arcuate band.
Figure 17B:
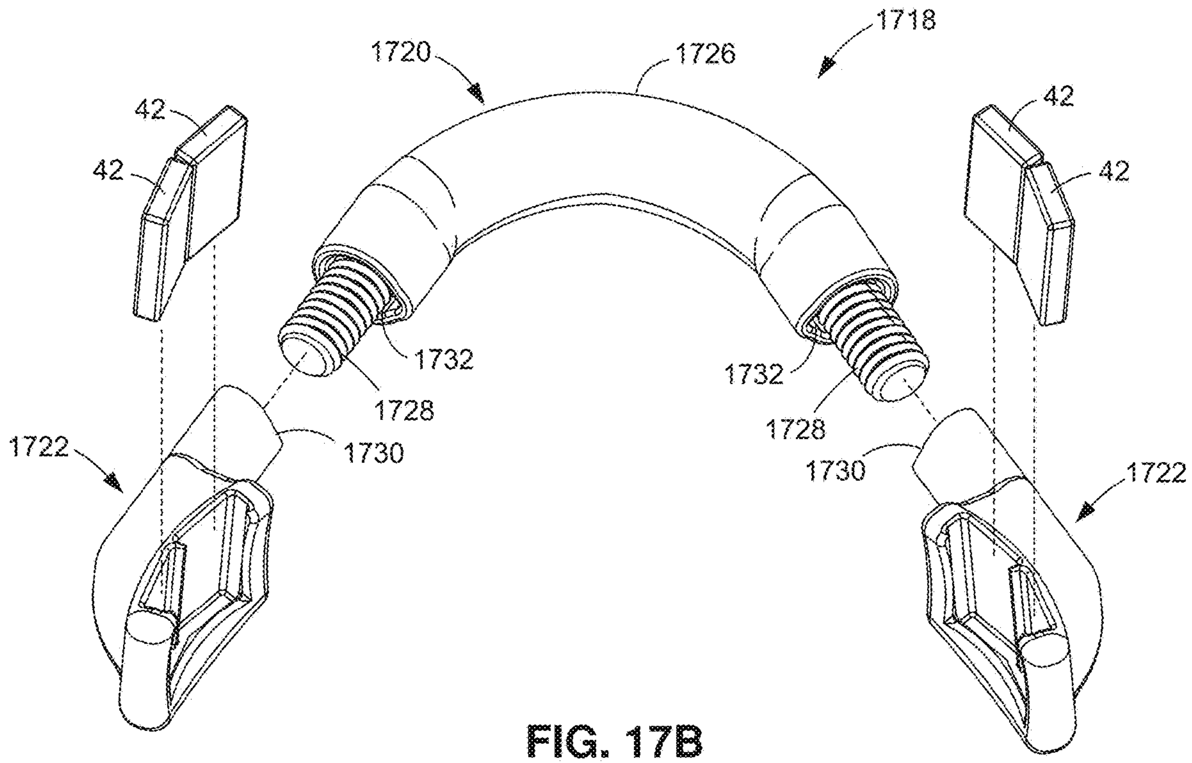
FIG. 17B is an exploded lower perspective view of the adjustable arcuate band of FIG. 17A.
Figure 17C:
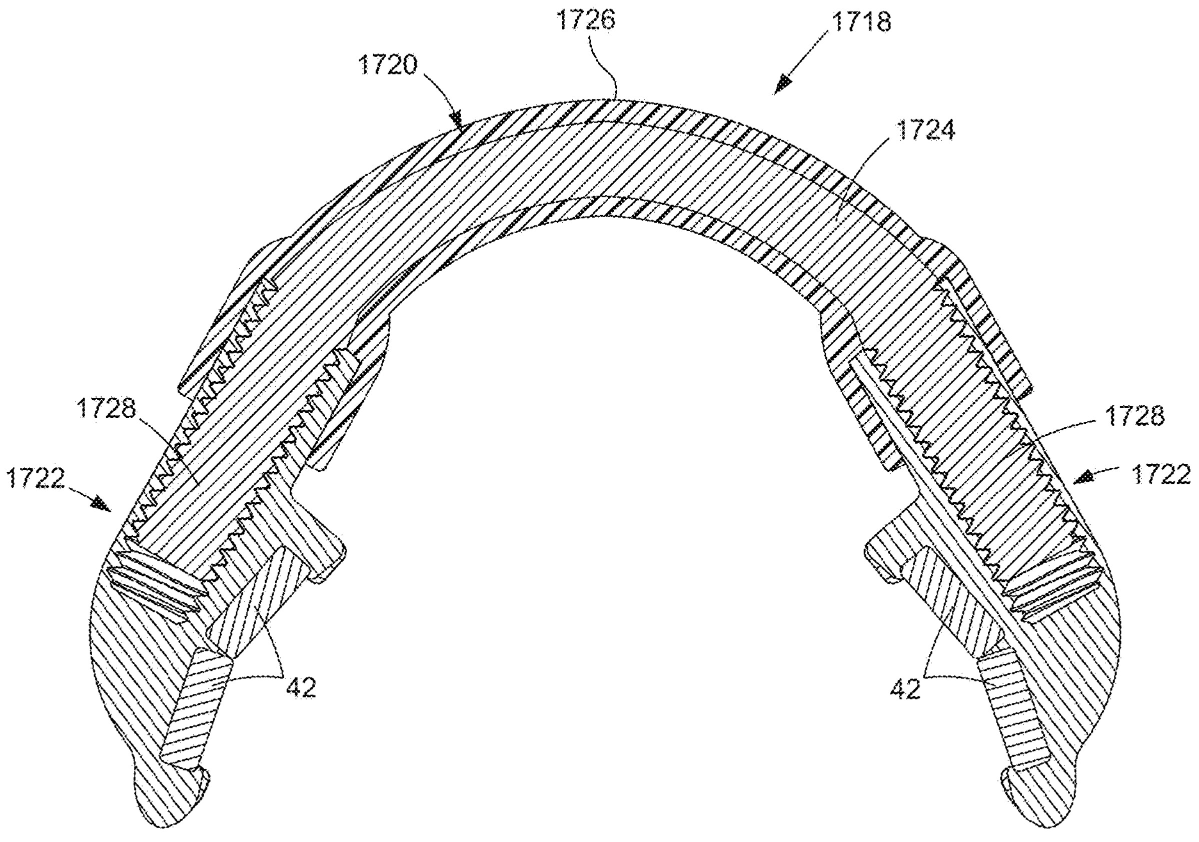
FIG. 17C is a cross sectional view of the adjustable arcuate band of FIG. 17A.
Figure 18A:
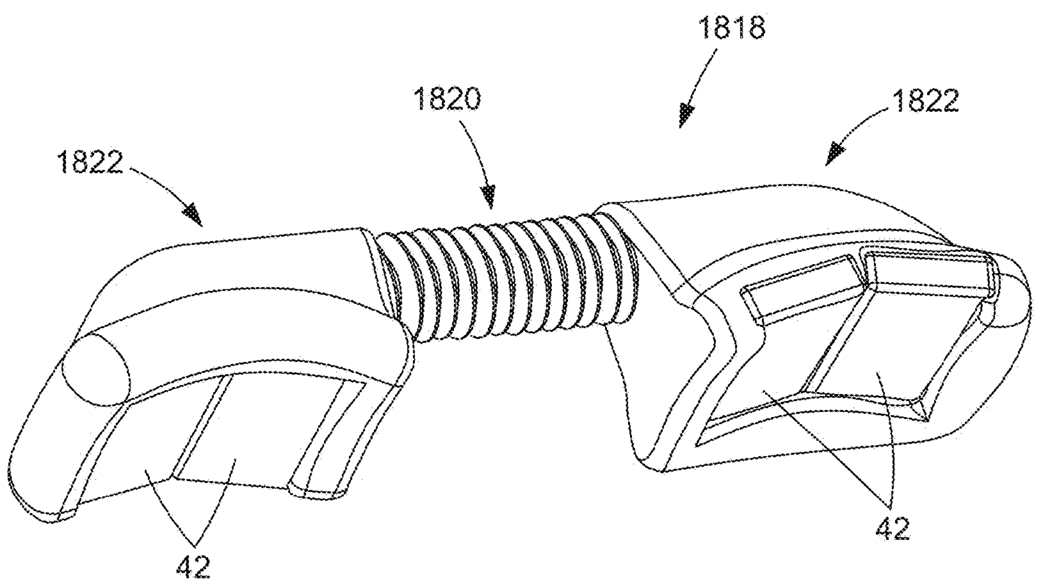
FIG. 18A is a side view of the adjustable linear band of FIG. 18A.
Figure 18B:
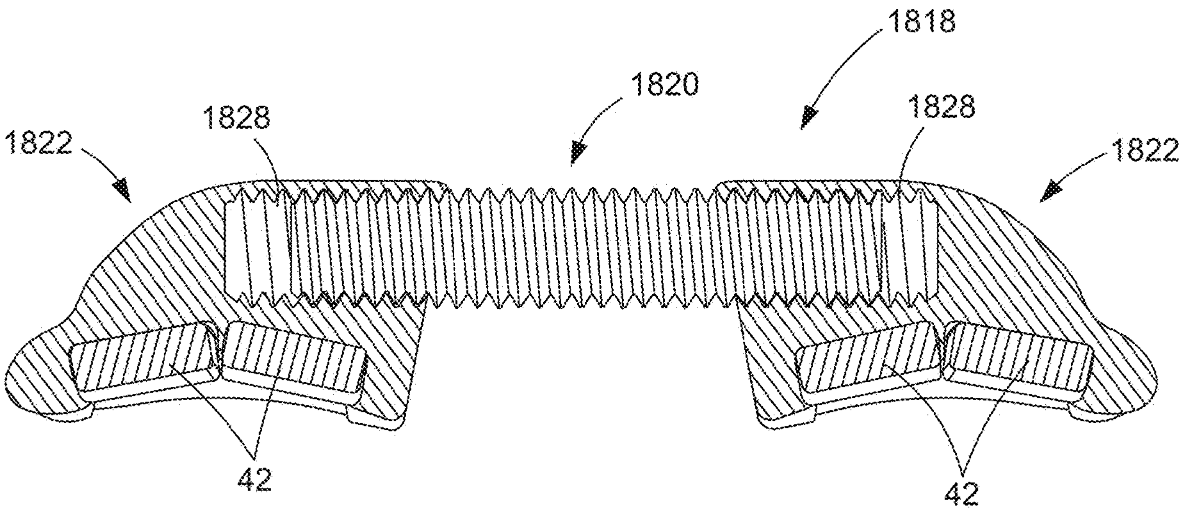
FIG. 18B is a lower perspective view of an embodiment of an adjustable linear band.

In addition to having adjustable distal portions to facilitate closing of an anatomical structure, certain implementations of the band enable selective size adjustment thereof to conform the band to the particular anatomical size of the user. FIGS. 17A-C show an arcuate band 1718 configured to facilitate size adjustment thereof, while FIGS. 18A-B show a linear band 1818 configured to facilitate size adjustment thereof. The arcuate band 1718 may be particularly suited for use as a nose band to dilate the user's nose airways, while the linear band 1818 may be particularly suited for use as a mouth closing mechanism. For more information regarding the use a band on the nose, please refer to U.S. Pat. No. 10,675,174, entitled BREATHING SYSTEM, the contents of which are expressly incorporated herein by reference.

The band 1718 is comprised of three primary components, including an arcuate central component 1720 and a pair of distal portions 1722, each being selectively attachable and adjustable relative to the arcuate central component 1720. According to one embodiment, the central component may include a rigid core 1724 that is of fixed configuration, namely, of a fixed arcuate configuration having a prescribed curvature and length. The central core 1724 may be covered by a layer of silicon, rubber, or other material that may provide comfort to the user. The central component may also be configured to include an apex 1726 at its midpoint, and a pair of connectors 1728 on opposite sides of the apex 1726. In the exemplary embodiment, each connector 1728 includes an externally threaded post configured to extend into a corresponding internally threaded recess on each distal portion 1722. However, it is understood that the configuration may be reversed, with the central component 1720 including internally threaded recesses on either end configured to engage with externally threaded posts on each distal portion 1722.

Each distal portion 1722 may include a cavity 1730 configured to receive a pair of magnets 42, as described in more detail above. Each distal portion 1722 may also include a connector 1730 configured to be cooperatively engageable with the connectors 1728 on the central component 1720.

To assemble the band 1718, the distal portions 1722 are screwed onto the connectors 1728 of the central portion 1720. Once the distal portions 1722 are engaged with the central portion 1720, the user may refine the size of the band 1718 by adjusting the position of the distal portions 1722 relative to the central portion 1720 via the threaded connection. For instance, rotation of the distal portions 1722 in a first rotational direction relative to the central component 1720 may result in the distal portions 1722 moving toward the apex 1726 to effectuate making the band 1718 smaller, while rotation of the distal portions 1722 in a second rotational direction relative to the central component 1720 may result in the distal portions 1722 moving away from the apex 1726 to effectuate making the band 1718 larger. In this regard, making the band 1718 larger may entail moving the distal portions 1722 away from the apex 1726 as well as increasing the distance between the distal portions 1722, while making the band 1718 smaller may entail moving the distal portions 1722 toward the apex 1726 as well as decreasing the distance between the distal portions 1722. In the exemplary embodiment, the central component 1720 includes a cavity 1732 around a proximal end portion of each connector 1728 that a portion of the distal portion 1722 may be received within when the distal portion 1722 is engaged with the central portion 1720. The degree to which the distal portion 1722 is received within the central portion increases as the size of the band 1718 decreases, and decreases as the size of the band 1718 increases. The size may be adjusted to conform to the particular anatomy of the user's nose, or to adjust a dilating force applied to the user's nose.

Referring now to FIGS. 18A and 18B, linear band 1818 includes a central portion 1820 that is linear (e.g., extends along an axis and does not include an arcuate configuration) and is configured to engage with a pair of distal portions 1822. The central portion 1820 may include a pair of connectors 1828 on each end region thereof. Indeed, in one embodiment, the central portion 1820 may include a single threaded shaft having a length sufficient to enable engagement with the distal portions 1822 on each end region thereof. Some of the central portion 1820 may be coated or covered with an outer layer to conceal an intermediate segment of the central portion 1820.

To assemble the band 1818, the distal portions 1822 are screwed onto the connectors 1828 of the central portion 1820. Once the distal portions 1822 are engaged with the central portion 1820, the user may refine the size of the band 1818 by adjusting the position of the distal portions 1222 relative to the central portion 1820 via the threaded connection, similar to the band 1718 described above.

Although the exemplary bands 1718 and 1818 do not include teeth on the distal portions, it is understood that in other embodiments, the bands 1718 and 1818 may include teeth. Furthermore, to that end, any feature shown or described in relation to any embodiment described herein may be integrated into any other embodiment, so long as such integration would not destroy the functionality associated with that embodiment.

While FIGS. 1-7 show tabs 16 configured for use as a pair (e.g., one tab 16 on top of the user's mouth and another tab 16 on the bottom of the user's mouth), FIGS. 19-29 shows another embodiment of a tab 200 configured for use individually. In this regard, the tab 200 includes a first region 202 configured for placement on one side of the mouth and a second region 204 configured for placement on an opposite side of the mouth. The tab 200 includes at least one pair of metallic elements 206, with one metallic element 206*a* being in the first region 202 and another metallic element 206*b* being in the second region 204. Thus, the single tab 200 may be suitable for use with the band 18 without any additional tabs. As such, a user may only need to peel and stick one tab instead of two.

Figures 19, 20, 21:
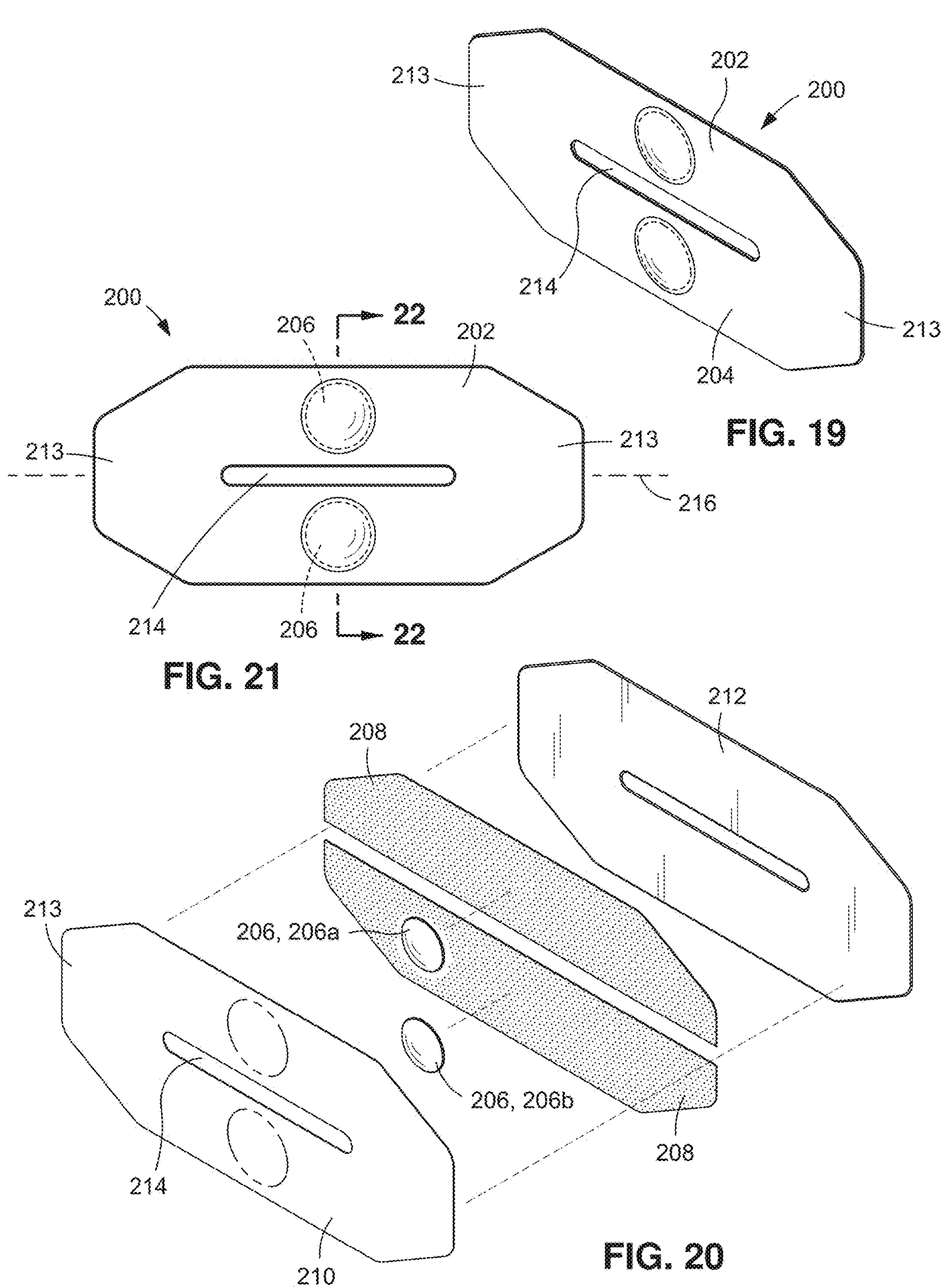
FIG. 19 is an upper perspective view of a one-piece tab having a pair of metallic elements.
FIG. 20 is an exploded upper perspective view of the one-piece tab depicted in FIG. 19.
FIG. 21 is a front view of the one-piece tab of FIG. 19.
Figures 22, 23:
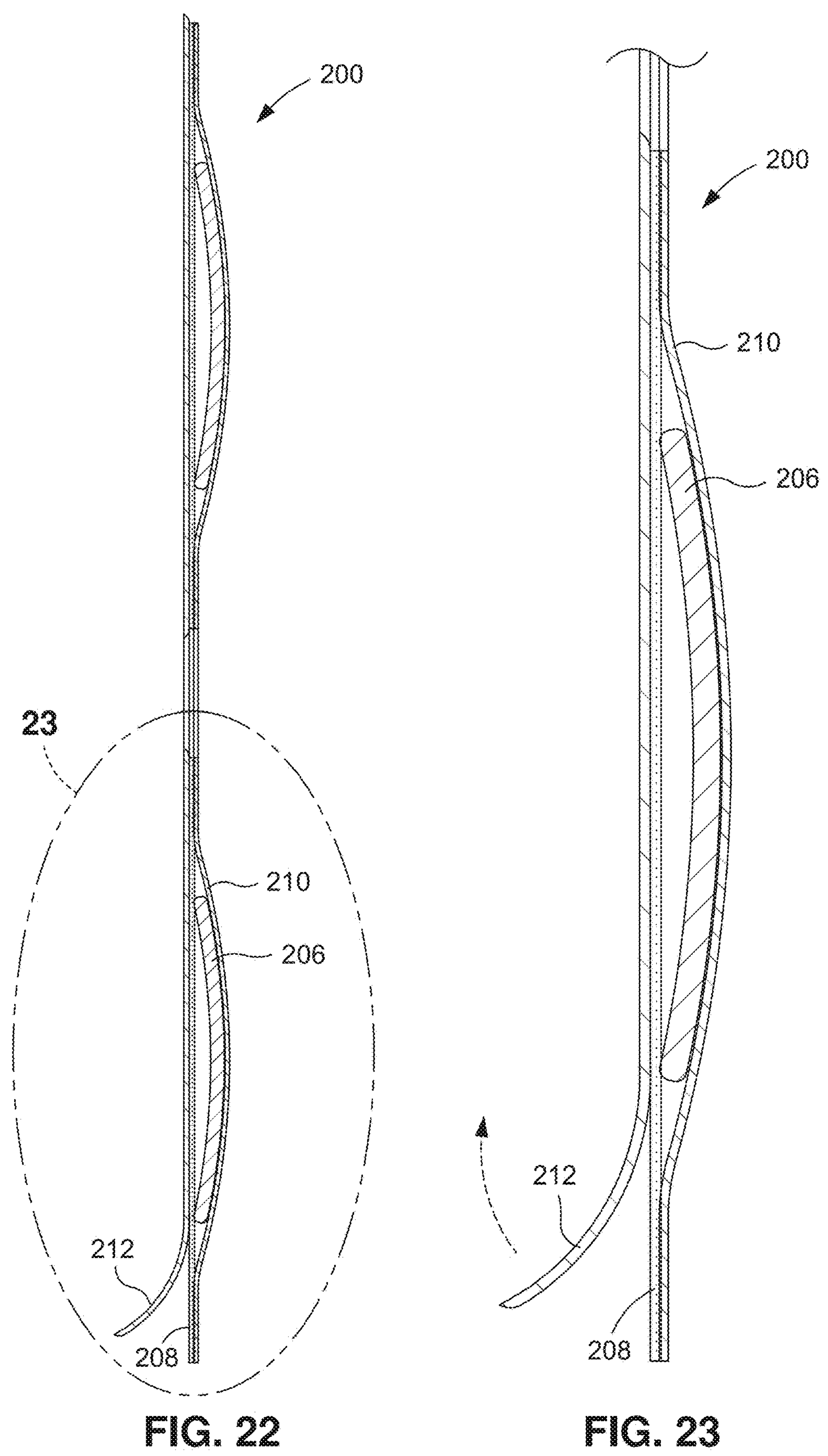
FIG. 22 is a side cross sectional view of the one-piece tab taken along line 22-22.
FIG. 23 is an enlarged side sectional view depicting a multi-layer construction of the one-piece tab.

As shown in FIGS. 20, 22, and 23, each tab 200 may be formed of a multi-layer construction, including an adhesive layer 208, a cover layer 210, and a peel-away layer 212. The adhesive layer 208 may include a first portion and a second portion, with the first portion corresponding to the first region 202 of the tab 200 and the second portion corresponding to the second region 204 of the tab 200.

The cover layer 210 may be a single layer that extends across both the first region 202 and the second region 204, as well as along lateral connecting regions extending between the first and second regions 202, 204. According to one embodiment, the cover layer 210 includes a slit 214 extending along a longitudinal axis 216 that extends between the pair of lateral portions 213. The first and second regions 202, 204 may be on opposite sides of the longitudinal axis 216. The slit 214 may be configured to generally extend along the intersection between the user's upper lip and lower lip, when installed, and may allow for a certain amount of flexing of the tab 200 while the tab 200 is adhered to the user, such as when a user may move his mouth when the band is not connected to the tab 200 (e.g., when talking, drinking water, yawning, etc.). This movement by the user, and corresponding flexing of the tab 200 may not destroy or reduce the adhesion of the tab 200 on the user.

The metallic elements 206 may be similar in configuration to the metallic elements described above. In the exemplary embodiment, the metallic elements 206 are captured between the adhesive layer 208 and the cover layer 210. In an alternative embodiment, the metallic elements 206 are on the other side of the adhesive layer 208, such that the adhesive layer 208 is between the metallic elements 206 and the cover layer 210.

Referring now specifically to FIGS. 22 and 23, the peel-away layer 212 may initially cover the adhesive layer 208, and may be peeled-away to expose the adhesive layer 208 prior to installation on the user.

FIGS. 24-26 show the tab 200 installed on the user, with the tab 200 extending over the user's mouth. In particular, the first region 202 is positioned over the user's upper lip, the second region 204 is positioned over the users lower lip and the slit 214 is positioned generally along the intersection of the upper and lower lips. This configuration positions metallic element 206*a* above the user's upper lip and metallic element 206*b* below the user's lower lip.

FIGS. 27-29 show the tab 200 coupled to the user, and a band 18 coupled to the tab 200. As can be seen, the band 18 is connected to the two metallic elements 206*a* b of the tab 200, and not to metallic elements in separate tabs.

Referring now to FIGS. 30-32, there is depicted another embodiment of tabs 300 specifically configured for use with user's having facial hair. In this regard, each of the tabs 300 may be elongate in configuration (e.g., having a length greater than a width) and configured to extend in a direction generally along one of the upper lip and the lower lip, to facilitate connection to the user, despite the facial hair. The longer configuration may provide greater adhesive area on each tab 300 to strengthen the connection to the user. The tab 300 may also be used of the thicker material than the tab 16 described above, to provide a more robust tab 300.

Other than the length and material, the construction of the tab 300 may be similar to the tabs described above, i.e., include a metallic element, a cover layer and an adhesive layer.

While the foregoing discusses the use of magnets to facilitate connection between the tabs and the band, it is contemplated that other fastening modalities known in the art may also be used without departing from the spirit and scope of the present disclosure. For instance, the tabs may include hook and loop fastening material (e.g., VELCRO) that engages with complementary hook and loop fastening material on the band. In this regard, the band may comprise a strip of fabric having the hook and loop material thereon, and which may have desired structural characteristics. In this regard, the fabric band may have limited elasticity to restrict opening of the user's mouth when the band is attached to the tabs. Other attachment modalities may also be used to fasten the band to the tabs. As such, in its broadest form, the tabs include a tab fastener, which may be a magnet, hook and loop fastener, clasp, button, snap fastener, etc., configured to engage with a corresponding band fastener to keep the user's mouth closed, or to perform another desired function, such as closing a wound.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A system for holding a portion of a user's body in a desired configuration, the system comprising:

a pair of metallic elements each being configured to be attachable to the user's body at respective first and second regions of the user's body; and a band having a main body and at least two magnets coupled to the main body, the main body having a middle portion, a pair of distal portions on respective sides of the middle portion, and a plurality of teeth integral to the main body and each tooth of the plurality of teeth being located at a respective one of the pair of distal portions to facilitate mechanical coupling with the pair of metallic elements, each tooth of the plurality of teeth extending away from an inner surface of a respective one of the pair of distal portions, at least one of the at least two magnets being coupled to a respective one of the pair of distal portions, each magnet being configured to be magnetically attractable to one of the pair of metallic elements, the band being configured to be coupled to the pair of metallic elements via a combination of a magnetic force and a mechanical force, the magnetic force being between the at least two magnets and the pair of metallic elements and the mechanical force being via engagement between the plurality of teeth and interface portions associated with the pair of metallic elements;

the pair of metallic elements and the band being configured to exert a force on the user's body to restrict separation of the first and second regions when the band is coupled to the pair of metallic elements.

2. The system recited in claim 1, wherein the plurality of teeth includes a first set of teeth positioned adjacent a first one of the at least two magnets and a second set of teeth positioned adjacent a second one of the at least two magnets.

3. The system recited in claim 1, wherein each interface portion includes a mesh material extending over a respective one of the pair of metallic elements and being configured to enable at least partial advancement of certain ones of the plurality of teeth therein.

4. The system recited in claim 1, wherein each interface portion includes a rubber material extending over a respective one of the pair of metallic elements and being configured to enable flexing in response to engagement with certain ones of the plurality of teeth.

5. The system recited in claim 1, wherein the band includes a pair of recesses formed in respective ones of the pair of distal portions, the at least two magnets include a first pair of magnets in a first one of the pair of recesses and a second pair of magnets in a second one of the pair of recesses.

6. The system recited in claim 1, wherein the pair of metallic elements are integrated into a single tab having a first region, a second region and a slit between the first region and the second region, a first one of the pair of metallic elements positioned in the first region and a second one of the pair of metallic elements positioned in the second region, the single tab having an adhesive to facilitate adhering of the tab to the user.

7. The system recited in claim 1, wherein each one of the pair of metallic elements being integrated into a respective one of a pair of tabs, each one of the pair of tabs having an adhesive to facilitate adhering of the tab to the user.

8. The system recited in claim 1, wherein the pair of distal portions of the band are moveable relative to each other to facilitate size adjustment of the band.

9. A method of applying a restrictive force to a user adjacent the user's mouth, the method comprising:

adhering a pair of metallic elements on opposite sides of the user's mouth; and magnetically and mechanically connecting a rigid band to the pair of metallic elements to facilitate application of a force on opposite sides of the user's mouth to restrict opening of the user's mouth, the magnetic connection being between at least two magnets of the rigid band and the pair of metallic elements and the mechanical connection being via engagement between a plurality of teeth of the rigid band and interface portions associated with the pair of metallic elements.

10. The method as recited in claim 9, wherein the adhering the pair of metallic elements includes adhering a single tab on the user's skin, the single tab including the pair of metallic elements.

11. The method as recited in claim 9, wherein the adhering the pair of metallic elements includes adhering a pair of tabs to the user, each of the pair of tabs including a respective one of the pair of metallic elements.

12. The method as recited in claim 9, further comprising the step of adjusting a size of the band by adjusting a distance between a pair of distal portions of the band.

13. A system for holding a portion of a user's body in a desired configuration, the system comprising:

a pair of tabs, each tab including a flexible body and a metallic element coupled to the flexible body, the flexible body having an adhesive on a surface thereof to facilitate selective attachment of the respective tab to the user's body, the pair of tabs being configured to be attachable to the user's body in spaced relation to each other; and a band having a main body and at least two magnets coupled to the main body, the main body having a middle portion and a pair of distal portions on respective sides of the middle portion, and a plurality of teeth formed at each distal portion of the pair of distal portions, at least one of the at least two magnets being coupled to a respective one of the pair of distal portions, each magnet being configured to be magnetically attractable to one of the pair of tabs to facilitate magnetic attraction;

the main body and the pair of tabs being configured to be mechanically coupled to each other when the at least two magnets of the band are magnetically coupled to the pair of tabs, the mechanical coupling including engagement between the plurality of teeth and an interface portion of each flexible body to strengthen the connection between the band and the pair of tabs and resist shear forces that are in a direction tangent to an outer surface of a respective one of the pair of tabs.

14. The system recited in claim 13, wherein each tooth of the plurality of teeth extends away from an inner surface of a respective one of the pair of distal portions, in a direction away from the at least two magnets.

15. The system recited in claim 14, wherein the flexible body includes a mesh material capable of enabling at least partial advancement of certain ones of the plurality of teeth therein.

16. The system recited in claim 14, wherein the flexible body includes a rubber material capable of flexing in response to engagement with certain ones of the plurality of teeth.

17. The system recited in claim 13, wherein the pair of distal portions of the band are moveable relative to each other to facilitate size adjustment of the band.

18. The system as recited in claim 14, wherein each of the plurality of teeth is tapered such that a cross-sectional area of the tooth decreases as the tooth extends away from the respective distal portion.

* * * * *